(12) United States Patent
Bendis et al.

(10) Patent No.: US 11,272,996 B2
(45) Date of Patent: Mar. 15, 2022

(54) METHODS AND DEVICES FOR PERFORMING SEQUENTIAL PROCEDURES UTILIZING A STANDARDIZED SYSTEM

(71) Applicant: REVITICELL HOLDINGS, INC., Jacksonville, FL (US)

(72) Inventors: Gregory G. Bendis, Jacksonville, FL (US); Leslie E. Frilling, Fruit Cove, FL (US); Arlene Silvergleid Bumb, Huntington Beach, CA (US)

(73) Assignee: REVITICELL HOLDINGS, INC., Jacksonville, FL (US)

( * ) Notice: Subject to any disclaimer, the term of this patent is extended or adjusted under 35 U.S.C. 154(b) by 0 days.

(21) Appl. No.: 16/593,013

(22) Filed: Oct. 4, 2019

(65) Prior Publication Data
US 2021/0100631 A1 Apr. 8, 2021

(51) Int. Cl.
*A61B 50/30* (2016.01)
*A61B 50/00* (2016.01)

(52) U.S. Cl.
CPC ...... *A61B 50/30* (2016.02); *A61B 2050/0056* (2016.02); *A61B 2050/3008* (2016.02); *A61B 2050/3011* (2016.02)

(58) Field of Classification Search
CPC . A61F 17/00; A61B 50/30; A61B 2050/0056; A61B 2050/3008
USPC ................................................ 206/570, 438
See application file for complete search history.

(56) References Cited

U.S. PATENT DOCUMENTS

| 5,707,331 A | 1/1998 | Wells et al. |
| 5,895,346 A | 4/1999 | Wells et al. |
| 6,129,761 A | 10/2000 | Hubbell |
| RE38,730 E | 4/2005 | Wells et al. |
| RE38,757 E | 7/2005 | Wells et al. |

(Continued)

FOREIGN PATENT DOCUMENTS

| WO | WO 2005/011569 | 2/2005 |
| WO | WO 2007/102635 | 9/2007 |

(Continued)

OTHER PUBLICATIONS

Harvest Terumo, Harvest® Adiprep® Adipose Concentration System brochure, Jan. 2014, pp. 1-4.

(Continued)

*Primary Examiner* — Steven A. Reynolds
(74) *Attorney, Agent, or Firm* — Saliwanchik, Lloyd & Eisenschenk

(57) ABSTRACT

The subject invention is a standardized system that provides for the methodical performance of a variety of procedures, which is designed to be configured as a variety of single-use devices, each in the form of a procedure kit which corresponds to a particular type of procedure, organized with all the exact components necessary to perform such particular type of procedure, in accordance with the included step-by-step instructions of a proprietary protocol with which such components correlate. This standardized system for performing a variety of procedures, and the methodical approach for performing each corresponding proprietary protocol, can improve the precision and efficiency of each procedure and, thereby reduce the chance of errors, minimize waste, increase productivity and provide for consistent outcomes.

29 Claims, 22 Drawing Sheets

(56) References Cited

U.S. PATENT DOCUMENTS

| | | | |
|---|---|---|---|
| 7,445,125 | B2 | 11/2008 | Ellsworth et al. |
| 7,699,766 | B2 | 4/2010 | Ellsworth et al. |
| 7,754,494 | B1 | 7/2010 | Verkaart et al. |
| 7,901,672 | B2 | 3/2011 | Fraser et al. |
| 7,922,972 | B2 | 4/2011 | Ellsworth et al. |
| 8,038,656 | B2 | 10/2011 | Lloyd et al. |
| 8,105,580 | B2 | 1/2012 | Fraser et al. |
| 8,119,121 | B2 | 2/2012 | Fraser et al. |
| 8,152,708 | B2 | 4/2012 | Ellsworth et al. |
| 8,348,887 | B2 | 1/2013 | Benoit et al. |
| 8,404,198 | B2 | 3/2013 | Amshey et al. |
| 9,044,547 | B2 | 6/2015 | Tremolada |
| 9,988,599 | B2 | 6/2018 | Bendis et al. |
| 2008/0050276 | A1 | 2/2008 | Bedingham et al. |
| 2010/0274205 | A1* | 10/2010 | Morelli ............... A61B 50/30 604/290 |
| 2011/0162438 | A1 | 7/2011 | Tokieda et al. |
| 2014/0186937 | A1 | 7/2014 | Smith et al. |
| 2014/0199770 | A1 | 7/2014 | Habrich et al. |
| 2015/0105754 | A1 | 4/2015 | Roche et al. |
| 2015/0291308 | A1* | 10/2015 | Irsch ............... B65D 43/021 206/508 |
| 2018/0273893 | A1 | 9/2018 | Bendis et al. |

FOREIGN PATENT DOCUMENTS

| | | |
|---|---|---|
| WO | WO 2011/145075 | 11/2011 |
| WO | WO 2013/030761 | 3/2013 |
| WO | WO 2013/132192 | 9/2013 |
| WO | WO 2013/181740 | 12/2013 |

OTHER PUBLICATIONS

Güven, S. et al., "Validation of an Automated Procedure to Isolate Human Adipose Tissue-Derived Cells by Using the Sepax® Technology," *Tissue Engineering: Part C*, 2012, vol. 18, No. 8, pp. 575-582.

Medikan International, Inc., "LipoKit II," www.medikanint.com/lipkit.html, 2011, p. 1-2.

Alexander, R.W. et al., "Autologous fat grafting: use of closed syringe microcannula system for enhanced autologous structural grafting," *Clinical, Cosmetic and Investigational Dermatology*, 2013, vol. 6, pp. 91-102.

Extended European Search Report, dated Apr. 2018, issued in related European Application No. 15835756.6, pp. 1-8.

\* cited by examiner

METHODS AND DEVICES FOR PERFORMING SEQUENTIAL PROCEDURES UTILIZING A STANDARDIZED SYSTEM

BACKGROUND OF INVENTION

Many processes and procedures are performed as a sequence of steps. Each step of such processes and procedures utilizes materials and techniques to achieve a particular outcome. In some cases, these steps can be performed in a different order, using different materials, or by using different techniques and a similar outcome can still be achieved. In some circumstances, however, it could be beneficial if the same sequence of steps were followed, and the same materials and techniques were used, each time a procedure was performed. By doing so, it would be more likely to achieve the same outcome each time the same type of procedure was to be performed, no matter who performs the procedure or where the procedure was performed. Further, such a methodical approach to performing a procedure could improve precision and efficiency, reduce errors, minimize waste, increase productivity and reduce costs.

The benefit of performing procedures with a methodical step-by-step sequence, and with materials and techniques specific to each step, would be even greater if the materials used were correlated with a protocol that was specific to each procedure. Using such protocols could ensure that the steps of each particular procedure were always conducted in the same sequence, using the same types and amounts of materials, and using essentially the same techniques every time such a procedure was performed. When performing a procedure according to a protocol in this manner, should an error occur, it would be easier to determine the factors that caused the error within the sequence of steps.

Regenerative medicine is a field of medical practice that utilizes biomaterials for patient treatments. It has been recognized that there is a lack of standardization in the field of regenerative medicine and a lack of consistency in the way that treatments are prepared for patient needs. The order of steps of various regenerative treatment preparation processes, the materials used, techniques, and other factors can vary. This lack of a methodical approach can inhibit the precise and efficient preparation of regenerative treatments. Also, the lack of consistency in the preparation of treatments for a particular patient can lead to inconsistent outcomes. This problem is not limited to the field of regenerative medicine. There are many other medical, quasi-medical, or even non-medical procedures that are not performed with an approach that is methodical and consistent.

It would be beneficial, therefore, if a standardized system could be configured to create a variety of single-use procedure kits. It would be advantageous if each type of procedure kit contained the type and quantity of materials necessary to perform a procedure, in accordance with the pre-determined steps of a specific protocol. It would be further beneficial if such a procedure kit provided for a discrete separation of the materials needed for each step of a protocol, and if the materials were organized to correlate with the protocol for the particular procedure being performed. Then, the user could select the appropriate procedure kit and methodically conduct the specific protocol required to successfully complete the procedure for which the procedure kit has been selected, with the expectation that the protocol could be conducted with precision and efficiency and that the desired outcome could be consistently achieved each time the same type of procedure kit was selected and used.

BRIEF SUMMARY

The subject invention provides a standardized system for the methodical performance of a procedure. The system can be configured in the form of a procedure kit, where each procedure kit can be configured for a particular procedure and be for single use. Each procedure kit can be organized with the materials necessary to perform a particular procedure, in accordance with the step-by-step instructions of a proprietary protocol. Such materials are referred to herein as "components," and can include, for example, tools, supplies, materials, solutions or any combination thereof, which are necessary to conduct one or more steps of the protocol for which the procedure kit has been configured.

Components can be discretely separated into cartridges contained within each procedure kit and each cartridge can be arranged within each procedure kit in an order that correlates with the proprietary protocol for the procedure to be performed. This standardized system, with the capability to be configured into various types of single-use procedure kits, and the methodical process of utilizing each procedure kit in accordance with a respective proprietary protocol, can improve the precision and efficiency of performing procedures, which can lead to a reduced chance of errors, minimization of waste, increased productivity, reduced costs, and a consistency of outcomes.

The outer layer of the procedure kit can contain the cartridges utilized for a procedure. Further, this outer layer, referred to herein as the "shell" of the kit, can include a handle so that the arrangement of cartridges can be carried as a unit. Before use, the shell of the kit can be opened to expose the ordered cartridges. After use, the shell of the kit can be closed, with any or all the used cartridges and any or all the used components inside their respective cartridges. The procedure kit can be resealed, and the entire procedure kit can be disposed of.

Each cartridge of a particular procedure kit contains the components necessary to conduct one or more steps of the proprietary protocol that corresponds to the procedure for which the procedure kit is configured. After a component has been used, it can be returned to the respective cartridge. When all the components, used or otherwise, have been returned to a particular cartridge, the cartridge can be placed back into the shell of the kit in the location from which it was removed. The predetermined arrangement of cartridges, and the organization of components within each cartridge, can significantly increase precision and efficiency when performing a procedure. Further, the process of removing cartridges from and return them to a respective position in a procedure kit, along with the ability to remove components from and return them to their respective cartridges, helps to ensure that all components have been used and are accounted for, which can lead to a decreased chance of errors.

Each procedure kit can also contain a rack that secures the cartridges. The rack can be of a modular design that corresponds with the design of the cartridges. In addition, the rack can accommodate one or more ancillary articles, such as, for example, preparation mats, syringe holders, or other components that may not fit in a cartridge. Cartridges and ancillary articles can be arranged in the rack in an order of use that correlates with a respective proprietary protocol, such that a starting point and ending point for the protocol can be discerned when observing the side-by-side arrangement of the cartridges.

When the shell of the kit is opened, the cartridges can be removed. Cartridges can include inserts designed to hold in place the components therein. There can also be specialized cartridges that are used in the process of conducting a protocol but are not specifically used to perform any particular step of such protocol. For example, a cartridge can be configured as a waste container for receiving and securely containing any waste materials that result when conducting a particular protocol. Advantageously, the inside of the shell of the kit, when opened, can provide a convenient surface or area for printed information and quick-reference instructions which can communicate, for example, the proper cartridge location, sequence of use, information about the contents of the cartridges and/or references to the step-by-step instructions of the protocol for which the procedure kit has been configured. Numbers, letters, symbols, color-coding schemes, or any combination thereof can be employed to enhance an understanding of the use of the procedure kit and to convey other information. Such information can be provided as a part of the shell of the kit, on cartridges, cartridge inserts, or any combination thereof.

The shell, cartridges, inserts, components, and ancillary articles in a procedure kit can be sterilized. The shell of the kit, cartridges, cartridge inserts, components and ancillary articles can be placed into one or more sterile barriers and, then, sterilized. Alternatively, the procedure kit, cartridges, inserts, components, ancillary articles, or any combination thereof, can be sterilized after the procedure kit is configured and placed within a sterile barrier, which is often referred to as "terminal sterilization." In embodiments where such terminal sterilization is used, after the sterile barrier is removed, the entire procedure kit can be placed in a sterile field.

Where the cartridges with components and/or inserts inside, and/or any ancillary articles, have each been placed in a sterile barrier and sterilized, only the sterile cartridges with components and/or inserts, and any ancillary articles, can be placed in a sterile field after each respective sterile barrier has been removed, but the procedure kit cannot. Alternatively, where components have been placed into sterile barriers and sterilized, only the components can be placed in a sterile field, after first being removed from each respective sterile barrier. Various layers of sterile barriers can be used to protect a procedure kit, so that it can be shipped, stored and, ultimately used in a sterile field. However, for some procedures, it may not be required that procedure kits, cartridges, components, ancillary articles, or any combination thereof, be placed in sterile barriers and sterilized.

A procedure kit of the subject invention can provide a repeatable methodology for preparing for and performing a specific protocol for a medical treatment for a patient in need of such treatment. Following the same order of steps and using the same type of components and techniques each time the protocol is prepared and conducted, can help standardize the preparation process for such treatment and can improve the precision and efficiency of treatment preparation which can, thereby, lead to a reduced chance of errors, increased productivity and consistency of outcomes, all of which can reduce patient risk.

This Brief Summary is provided to generally introduce one or more select concepts, in a simplified form, as further described below in the Detailed Disclosure. This Summary is not intended to identify key and/or required features of the claimed subject matter. Other aspects and further scope of applicability of the disclosed invention will also become apparent from the detailed descriptions given herein. It should be understood, however, that the detailed descriptions, while indicating various embodiments of the invention, are given by way of illustration only, since potential changes and modifications within the spirit and scope of the invention will become apparent from such descriptions.

BRIEF DESCRIPTION OF DRAWINGS

In order that a more precise understanding of the above recited invention can be obtained, a more particular description of the invention briefly described above will be rendered by reference to specific embodiments thereof and/or illustrated in the appended drawings. The drawings presented herein and appended hereto may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which.

DETAILED DISCLOSURE

Figure 1:
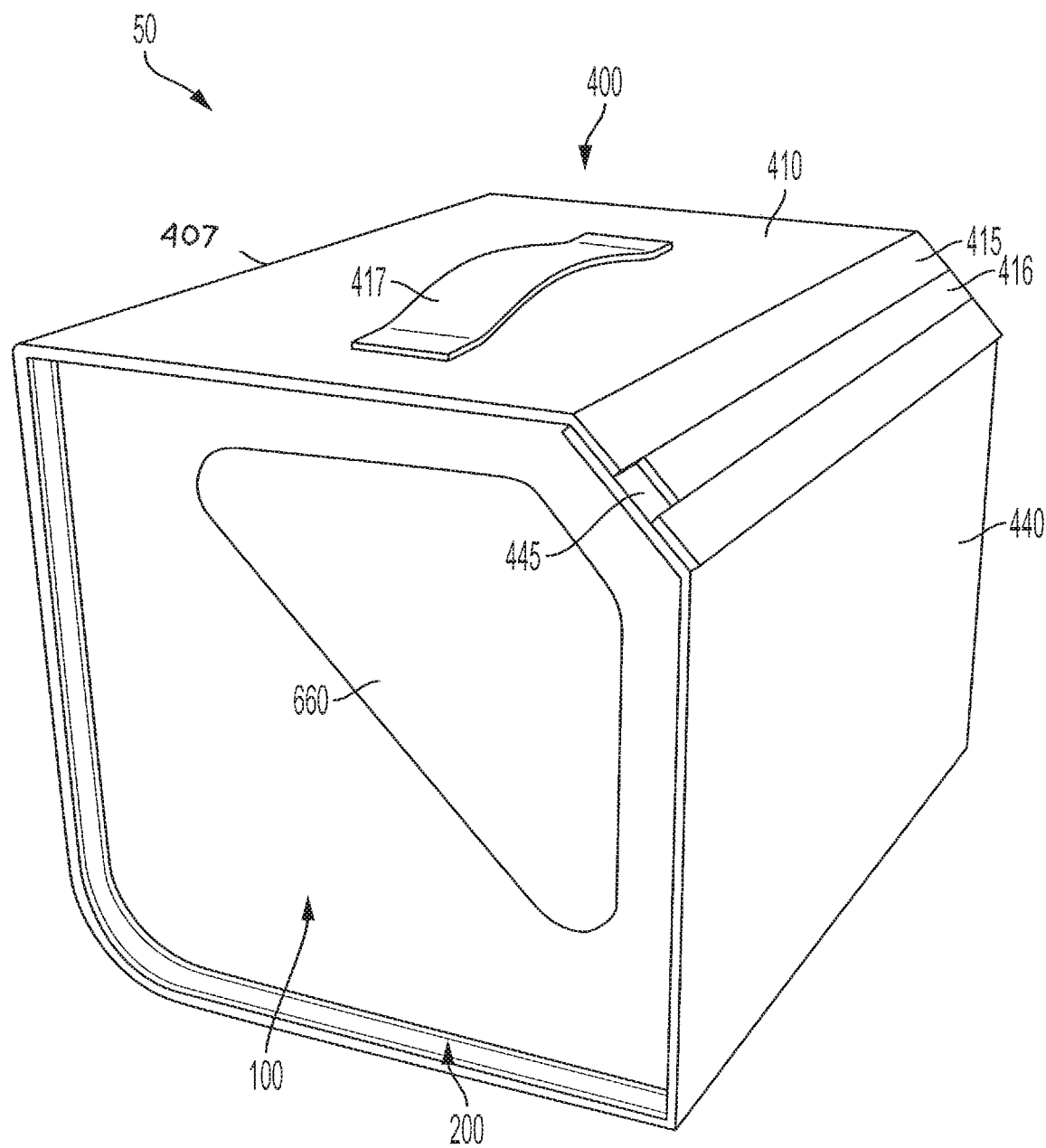
FIG. 1 shows a front, left-perspective view of an embodiment of an unopened procedure kit. In this embodiment, a cartridge can be a sidewall of the procedure kit.

The subject invention pertains to a standardized system for the methodical performance of medical, quasi-medical, or non-medical procedures. More specifically, embodiments of the subject invention provide a modular a single-use procedure kit, which contains the components necessary to perform a specific medical, quasi-medical, or non-medical procedure. The modularity of the subject invention is provided in that the procedure kit can be organized with one or more cartridges, each of which contains one or more of the components necessary to perform one or more steps of a proprietary protocol that corresponds to the procedure for which a particular procedure kit is configured. The modular design of the invention allows the arrangement of the cartridges within each procedure kit, and the organization of the components within each cartridge, to provide a methodical approach to performing a procedure. The invention also provides for the configuration of a variety of procedure kits because the modularity of the system allows for the arrangement of cartridges of different sizes and the organization of a variety of components within each cartridge, without changing the overall design or basic structure of the kit. Such a standardized system for, and methodical approach to, performing procedures can improve precision and efficiency, which can result in a reduction in the chance of errors, minimization of waste, increased productivity and outcomes that are consistent each time a particular procedure is performed.

The following description will disclose that the subject invention is particularly useful in the preparation of treatments in the field of regenerative medicine, where biomaterials are used for treatment. However, any person who performs procedures that require the skill of using various materials, in certain amounts, and with particular techniques, would recognize numerous uses for the subject invention that are not of a medical nature. Thus, while the subject application describes, and many of the terms and examples herein relate to, a medical use, in particular for preparing biomaterials, other uses and configurations of the invention, apparent to a person with skill in the art having benefit of the subject disclosure, are within the scope of the subject invention.

As used herein, the terms "about" or "approximately" are defined as meaning at least as close to a given value at either end of a range as is necessary to cover manufacturing variances, equipment tolerances, and normal variances in materials, as understood by those skilled in the art. More specifically, the terms "about" or "approximately" when used with quantitative aspects of the invention imply that absolute accuracy is not required with respect to those aspects for the invention to operate. In particular, when the terms "about" or "approximately" are used to describe a quantitative aspect of the invention, the relevant aspect may be varied by up to 110% (e.g., ±1%, ±2%, ±3%, ±4%, ±5%, ±6%, ±7%, ±8%, ±9%, or ±10%).

The term "procedure" as used herein is merely for literary convenience. The term should not be construed as limiting in any way. The devices, apparatuses, methods, techniques and/or aspects of the subject invention could be utilized for any process performed as a series of steps, phases, or the like, which can encompass medical, quasi-medical, or non-medical uses.

The term "component" is also used herein for literary convenience to describe any instrument, tool, material, ingredient, or other items that may be contained in a cartridge.

Likewise, the term "ancillary article" which is used herein for literary convenience to describe any instrument, tool, material, ingredient, or other item that can be contained in a procedure kit, typically engaged with a rack, but is not located in a cartridge.

Also, as used herein, and unless otherwise specifically stated, the terms "operable communication," "operable connection," "operably connected," "cooperatively engaged" and grammatical variations thereof mean that particular elements are connected in such a way that they cooperate to achieve their intended function or functions. The "connection" or "engagement" may be direct, or indirect, physical or remote.

It is to be understood that the figures and descriptions of embodiments of the subject invention have been simplified to illustrate elements that are relevant for a clear understanding of the invention, while eliminating, for purposes of clarity, other elements that may be well known in the art. Those of ordinary skill in the art will recognize that other elements may be desirable and/or required in order to implement the subject invention. However, because such elements are well known in the art, and because they do not facilitate a better understanding of the subject invention, a discussion of such elements is not provided herein.

Finally, reference is made throughout this application to "top" and "bottom," which generally means that the top faces up when the article is placed on a horizontal surface and the bottom faces down. For example, an embodiment of a procedure kit of the subject invention has a shell with top panel that opens upward and a bottom panel on which the procedure kit can sit when on a horizontal surface. For the sake of consistency, the orientation of the top and bottom of the one or more cartridges within an embodiment of a procedure kit are described as they are arranged, in a side-by-side vertical orientation, in the shell. Thus, when in a procedure kit, the lid of a cartridge faces left and the right side of the cartridge faces up.

Reference is made throughout this disclosure to the attached figures, numerals on the attached figures, and to indicate specific features related to these figures. When the same numeral is used on different figures, such use is intended to indicate the same or similar features for all the figures where the same numeral is used. With reference to the attached figures, which show examples of certain aspects of various embodiments of the subject invention, it can be seen that a procedure kit, or kit 50 of the subject invention comprises at least one, but typically a plurality of cartridges 100, which are arranged to fit side-by-side in a rack 200. Certain embodiments can also include one or more ancillary articles 500. The rack, plurality of cartridges, and ancillary articles can be at least partially enclosed within a shell 400 of the procedure kit 50.

Figure 2:
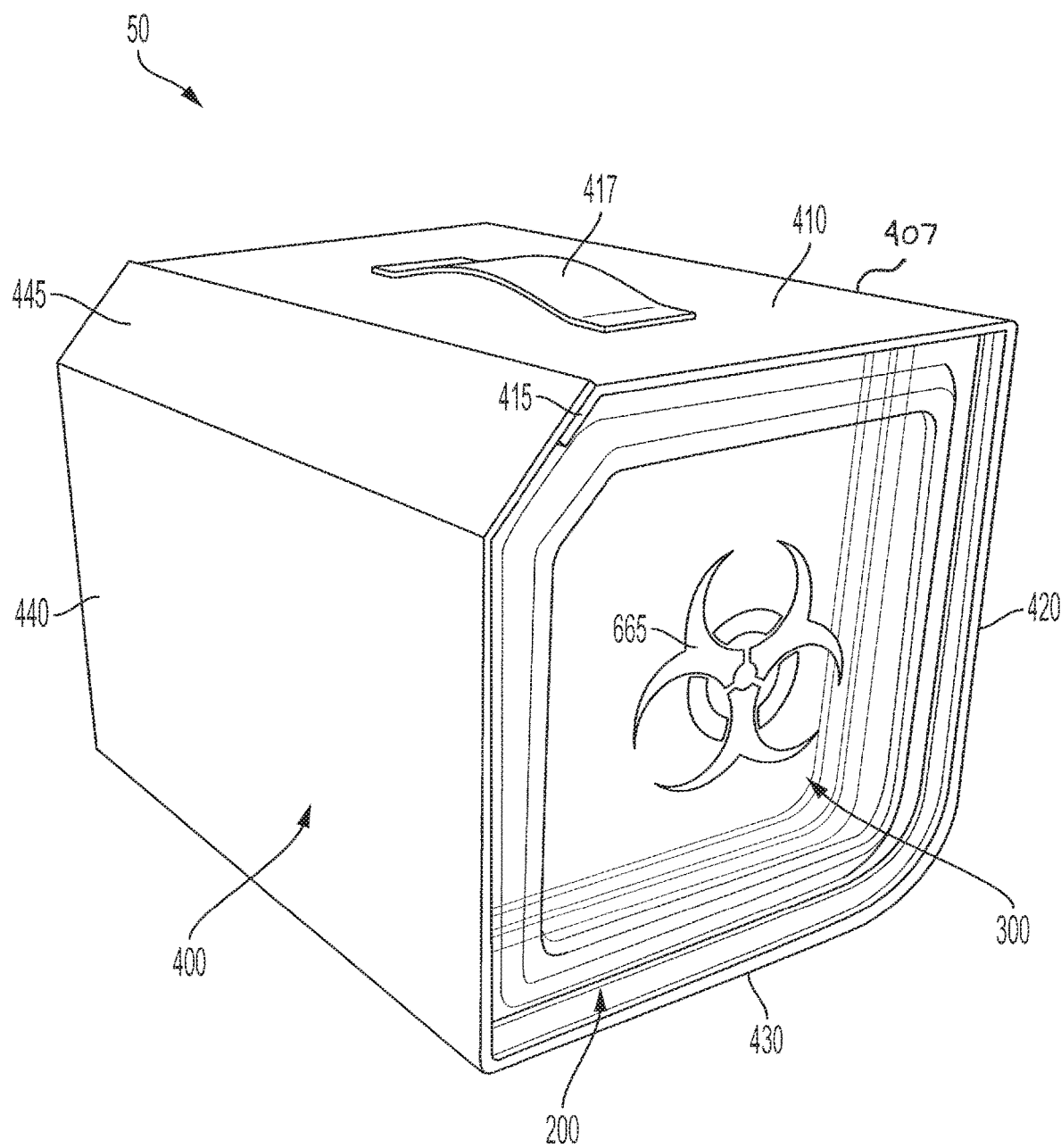
FIG. 2 shows a front, right-perspective view of an embodiment of a resealed procedure kit. In this embodiment, a cartridge, for example, in the form of a biohazard cartridge, can be seen as a sidewall of the procedure kit.
Figure 3:
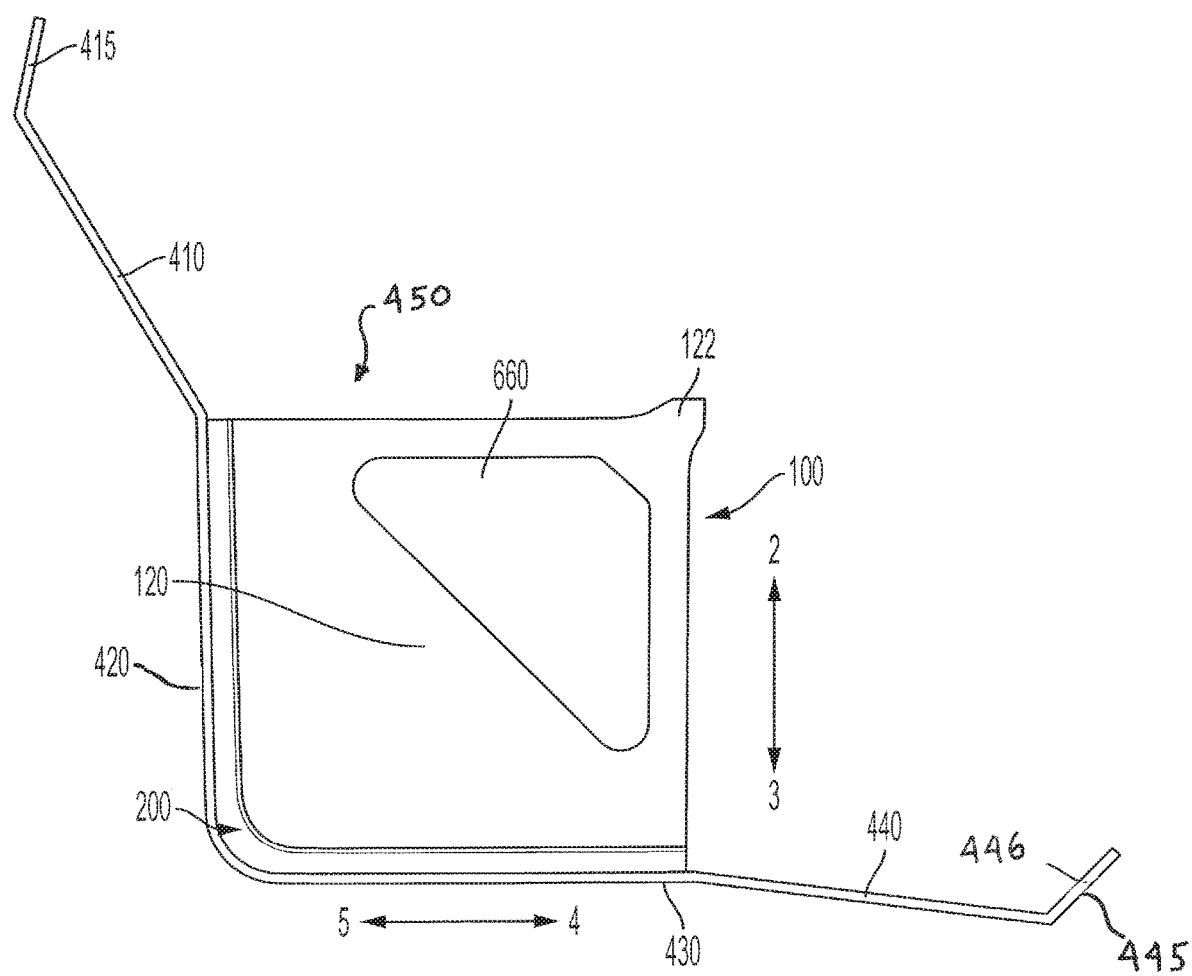
FIG. 3 shows a left-side elevation view of an embodiment of an opened procedure kit.

One embodiment of the subject invention can be seen in FIGS. 1 and 2, which shows the shell 400 forming a partial enclosure for a plurality of cartridges 100 arranged in the procedure kit 50. The side-by-side arrangement of cartridges in the rack 200 can be seen, for example, in FIGS. 5A, 5B, 6 and 7. Each cartridge in the procedure kit can contain one or more of the components 700 utilized to conduct one or more steps of a proprietary protocol that corresponds to a particular procedure for which the kit 50 is configured. Components can include, for example, any of a variety tools, supplies, materials, solutions or other items. By way of a non-limiting example, a blood-preparation protocol for an orthopedic procedure can include using a first cartridge containing components needed to set up the sterile field; a second cartridge containing syringes prefilled with anticoagulant, a butterfly needle, a tourniquet, gauze, and an adhesive bandage; a third cartridge containing transfer hubs and preparation syringes; and, an ancillary article 500 which can be, for example, a stand for supporting the syringes.

Figure 5A:
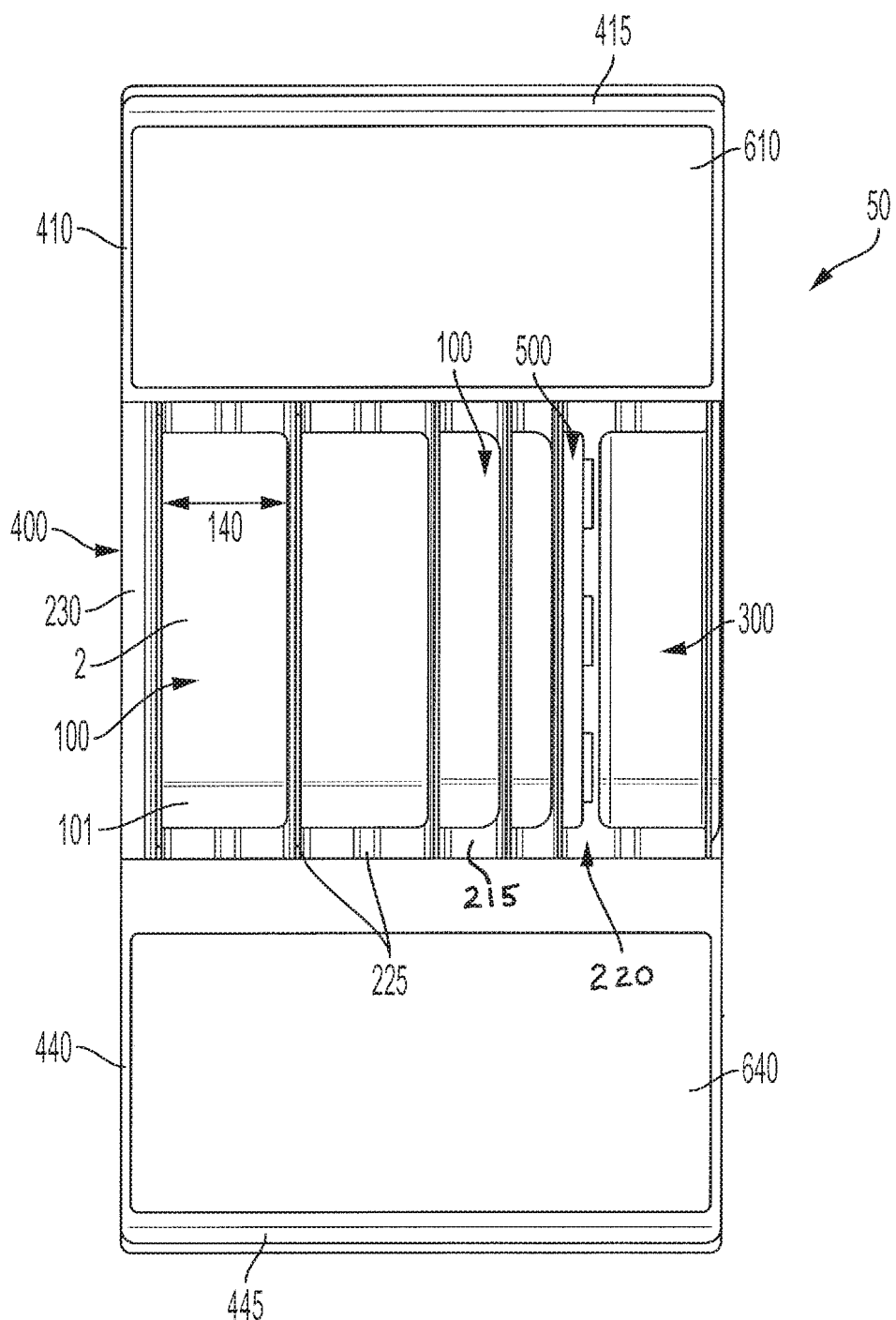
FIG. 5A shows a top-plan view of an embodiment of an opened procedure kit.
Figure 5B:
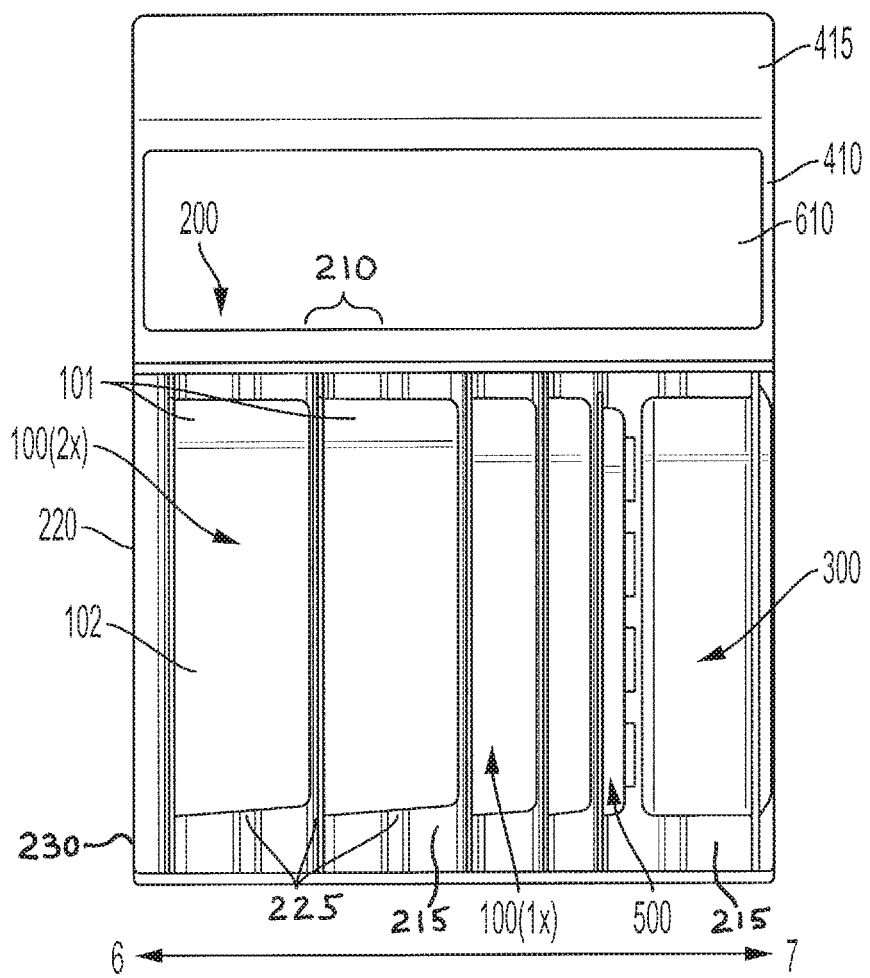
FIG. 5B shows a front-elevation view of an embodiment of an opened procedure kit.
Figure 6:
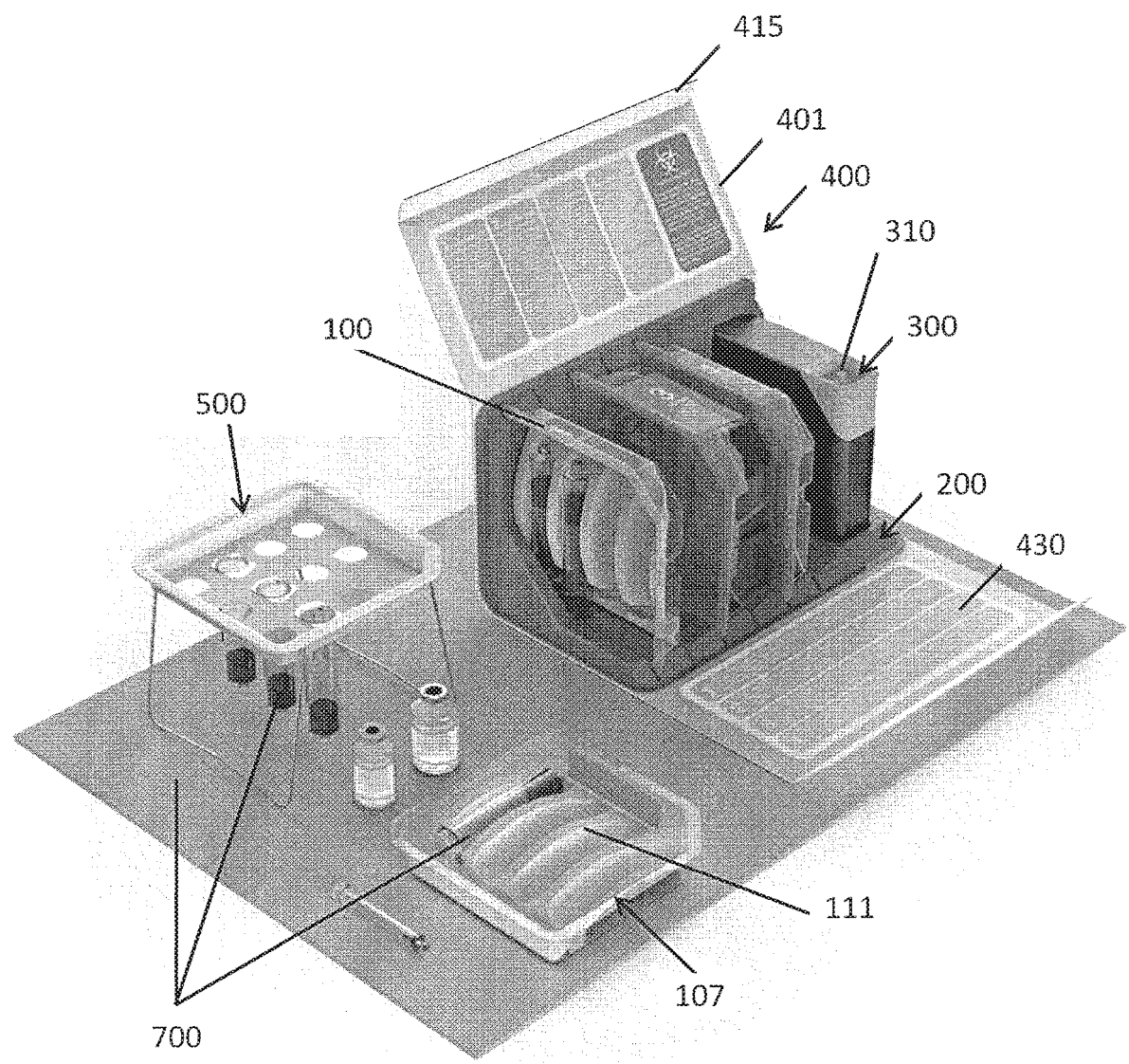
FIG. 6 shows an embodiment of a procedure kit in use with an opened cartridge and an ancillary article arranged for use with the components.
Figure 7:
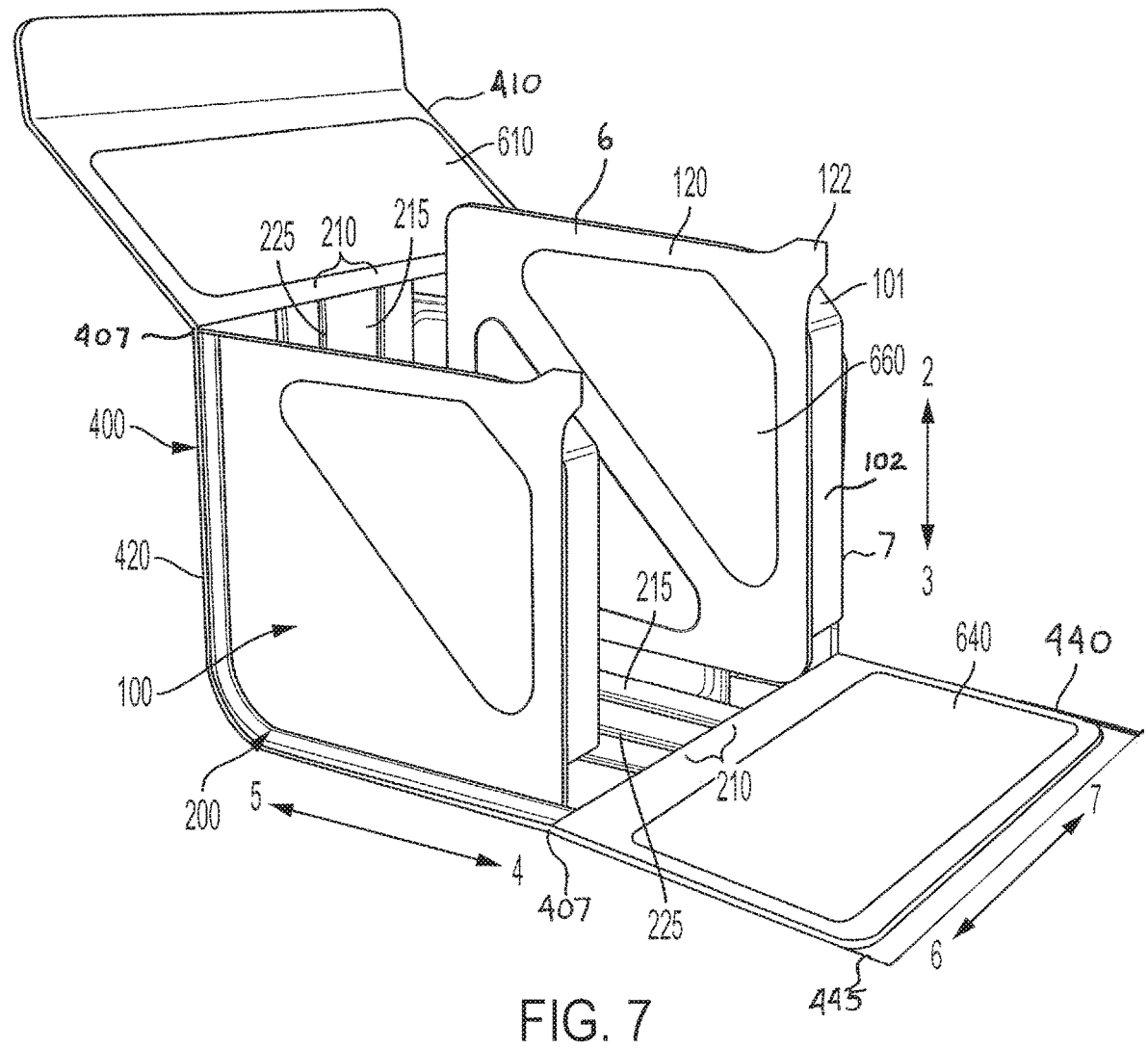
FIG. 7 shows an embodiment of an opened procedure kit and a cartridge partially removed from the rack. Also shown is a cartridge at the left side of the rack that, in this embodiment, functions as a sidewall.

One embodiment of a procedure kit 50 with the shell 400 opened is shown in FIGS. 3, 4, 5A, 5B 6 and 7. As used herein, the numeral 2 indicates top, the numeral 3 indicates bottom, the numeral 4 indicates front and the numeral 5 indicates back. In FIG. 7 and in other Figures, the numeral 6 indicates left and the numeral 7 indicates right. Thus, shown in FIG. 7, numerals 2, 3, 4, 5, 6 and 7 all relate to the orientation of the procedure kit, and the cartridges or ancillary articles as positioned therein, when the procedure kit is positioned on a horizontal surface.

In one embodiment, the shell 400 of the kit 50 has a top panel 410 from which extends or connects an unseal flap 415. In a further embodiment, the unseal flap incorporates an unseal mechanism 416 used to unseal the unseal flap to open the kit. When the unseal flap is unsealed with the unseal mechanism, the top panel can be rotated upwards or otherwise displaced to provide access to the cartridges inside the kit. Ideally, an unseal mechanism is configured for one-time use, such that once utilized to open a kit, the unseal mechanism and the unseal flap are disabled or otherwise incapable of being used to reseal the kit. By way of example, an unseal mechanism can be an unseal strip that can be pulled to rip away a section of the unseal flap. By way of another example, an unseal mechanism can be a break-away snap or piece of material that becomes disabled or broken when utilized to open the kit. In yet another example, an unseal mechanism can be an adhesive strip that can be torn or ripped to open the unseal flap.

In one embodiment, the shell 400, containing the one or more cartridges 200, is formed from multiple, connected panels. There can be top panel 410 that connects to, or is an extension of, a back panel 420 which, in turn, can connect to, or be an extension of, a bottom panel 430. The bottom panel can, in turn, connect to, or be an extension of, a front panel 440 from which can extend, or be connected, a reseal flap 445. The reseal flap can incorporate a reseal mechanism 446. In one or more embodiments, these panels and flaps operably connect along one or two edges to form an at least partially enclosed storage compartment 450 for containing the plurality of cartridges 100 arranged in the procedure kit 50, and for any ancillary articles 500 that may also be contained therein.

In another embodiment, the shell 400 of the kit 50 is comprised of one or more lengths of material that are folded or otherwise configured into the panels and flaps described above. With this embodiment, a complete procedure kit, before the shell is opened, can have the top panel 400 down and going over the top 2 of the cartridges 100. Alternatively, the top panel can be resting on the top 2 of the cartridges. This embodiment can further have the front panel up and also, either going over the front side 4 of the cartridges or resting against the front side 4 of the cartridges.

Figure 4:
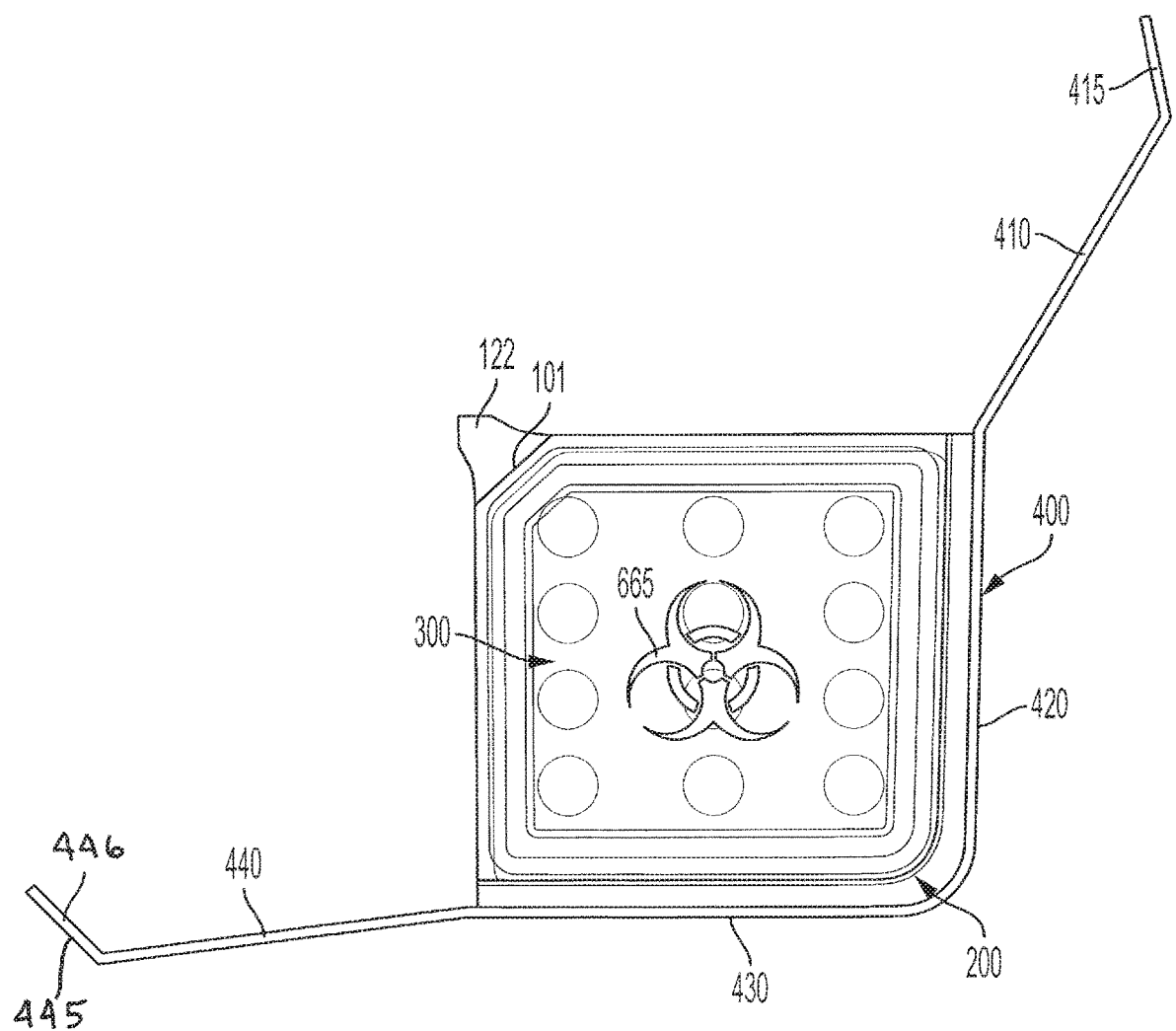
FIG. 4 shows a right-side elevation view of an embodiment of an opened procedure kit.

As will be discussed in more detail below, a cartridge 100 can have an angled wall 101 between the top side 2 and the front side 4, forming a flattened corner section, as shown, for example, in FIG. 4. In a further embodiment, the shell 400 has an unseal flap 415 and a reseal flap 445 such that, when the shell is unopened, the unseal flap is secured to the outside of the reseal flap and the reseal flap is either going over or resting on the angled wall 101 of the cartridges. FIG. 1 shows an embodiment of a procedure kit 50 prior to being opened, with the unseal flap 415 over the reseal flap 445.

To reseal the shell 400 of the kit 50, the top panel can be moved down over the top 2 end of the kit and either goes over or is resting on the top 2 of the cartridges 100, the remaining portion of the unseal flap 415 can be moved down over the angled wall 101 of the cartridges, the front panel can be moved up so that it either goes over or is resting against the front 4 of the cartridges, and the reseal flap 445, extending from the front panel 440, can be directed onto the unseal flap, so that the reseal flap can be secured to the outside of the unseal flap with a reseal mechanism 446. Any of a variety of reseal mechanisms, known to those with skill in the art, can be so reseal a used kit. By way of example, a reseal mechanism can be an adhesive strip, snaps, hook and loop material, a one-way insert, some combination thereof or other mechanisms or techniques known in the art. FIG. 2 shows an embodiment of a procedure kit after being resealed with a reseal mechanism 446. In one embodiment, both before the shell of the kit is opened, and after it is resealed, the left and right side of the procedure kit are at least open or partially unenclosed. With this embodiment, the leftmost cartridge and rightmost cartridge contained in the kit can be seen.

A shell can comprise any of one or more materials, such as, by way of non-limiting examples, pasteboard, cardboard, plastic, nylon, woven or non-woven cloth, metal, glass, PTFE foam, acrylic, ceramic, wood, and other materials or combinations thereof. The material chosen can depend upon a variety of factors including, but not limited to, the number of cartridges to be contained in the shell, whether the kit is to be sterilized, the sterilization technique(s), disposal method(s), where the kit may be used, and other factors understood by those with skill in the art. It is within the skill of a person trained in the art to determine the appropriate one or more materials suitable for a procedure kit.

In certain embodiments, the shell 400 of the kit 50 has a handle 417 that is a part of or attached to the top panel 410. In further embodiments, the shell 400 can be opened by removing the unseal strip 416, and lifting or rotating the top panel. In still further embodiments, the front panel 440 is also lowered to provide access to the interior. FIGS. 3, 4, 5A, 5B, 6 and 7 show, for example, a top panel that is folded up and backward with the connection between the top panel and back panel 420 acting as the hinge-point 407. Opening the top panel allows the cartridges, and other items in the procedure kit to be pulled up and out of the procedure kit. A top panel can be connected to a back panel by any of a variety of hinges known in the art. The top panel can, alternatively, be a continuation of the back panel, which is configured to fold at the hinge-point 407 which would be the connection point between the top panel and back panel. With respect to the front panel, FIGS. 3, 4, 5A, 6 and 7 show, for example, a front panel that can be folded down to lay in front of the kit, with the connection between the front panel and bottom panel 430 configured as the hinge-point 407. Opening the front panel allows the items in the procedure kit to be pulled forward and out of the procedure kit. A front panel can be connected to a bottom panel by any of a variety of hinges known in the art, or the front panel can be a continuation of the bottom panel, which is configured to fold at a hinge-point 407 which would be the connection point between the front panel and bottom panel, such as shown, for example, in FIGS. 3, 4, and 7.

In one embodiment, a cartridge 100 arranged at the left side 6 of the rack 200 functions as a left sidewall to the otherwise partially open left side of the procedure kit 50. One example of this is shown in FIG. 1. In a further embodiment, a cartridge arranged at the right side 7 of the rack functions as a right sidewall to the otherwise partially open right side of the procedure kit. One example of this is shown in FIG. 2. In a particular embodiment, an example of which is shown in FIG. 2, the cartridge acting as a left or right sidewall is a waste cartridge 300. In a specific example, a waste cartridge is configured to be a biohazard cartridge.

In one or more embodiments, the shell 400 of the kit 50 has an unseal flap 415 that secures the contents of the unopened procedure kit 50. In a further embodiment, the unseal flap includes an unseal mechanism, such as, for example, an unseal strip 416, which is removed from the unseal flap to allow the top panel 410 and the front panel 440 to be opened. The presence of an intact unseal flap 415 can indicate that the procedure kit is new or has not been used or tampered with. In a further embodiment, the presence of the unseal mechanism indicates that the contents of the procedure kit are sterile. In certain embodiments, the unseal flap, once opened, cannot be reused to close the kit. Thus, once the unseal mechanism is used to unseal an unseal flap, neither can be used to reseal the shell of the kit. Any of a variety of unseal mechanism devices and techniques can be used to unseal an unseal flap. By way of example, an unseal mechanism can be an unseal strip that can be pulled to rip away a section of the unseal flap, a break-away snap or material that becomes disabled or broken when the unseal flap is utilized to open the kit, or an adhesive strip that can be torn or ripped to open the unseal flap. Zip strips or tear-away seals, for example, can be particularly advantageous for use as an unseal mechanism because they are typically easy to remove. A person of skill in the art would be able to determine an appropriate type of unseal mechanism.

Once a procedure kit has been opened and used to conduct the proprietary protocol that corresponds to the procedure for which a particular of procedure kit is configured, the used cartridges, with any of the used components inside, any used ancillary articles, and any used waste cartridges can be returned to the rack 200, and the shell 400 of the kit 50 can then be resealed so that the procedure kit with the used contents can be properly disposed of. In one or more embodiments, the shell of the kit has a reseal flap 445 that secures the contents of the procedure kit 50 after the shell 400 of the kit has been closed. To make such securement possible, a variety of reseal mechanisms 446 devices and techniques can be used to engage the reseal flap to the shell of the kit. For example, an adhesive strip, hook-and-loop material, snaps, one-way pins or inserts, or other types of reseal mechanisms can be arranged on the reseal flap. Other types of reseal mechanisms can also be used. A person of skill in the art would be able to determine an appropriate type of unseal mechanism. The absence of an intact unseal flap 415 and, in a reseal flap over the unseal flap, which has been engaged to reseal the shell of the kit, can indicate that the procedure kit 50 has been opened and can further indicate that it should not be used. Further, the presence of a waste cartridge 300, such as a biohazard cartridge, visible at one or the other side of the closed procedure kit, can provide a clear indication that a resealed shell of the kit may include biohazard materials and should be handled with appropriate precautions. In a particular embodiment, a waste cartridge is located and is visible from the right side 7 of a kit. Waste cartridges are described in more detail below.

Figure 8A:
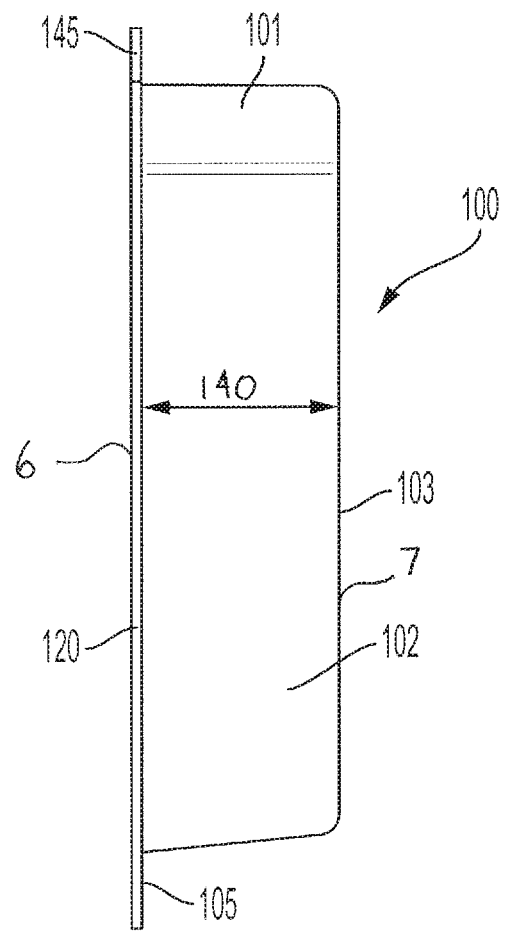
FIG. 8A shows a front elevation view of one embodiment of a cartridge, as it would be oriented when positioned in a rack. In this embodiment, an angled corner is located at the corner between the top wall and front wall of the cartridge. The back side can be a mirror image of the front side, but without the angled corner.
Figure 8B:
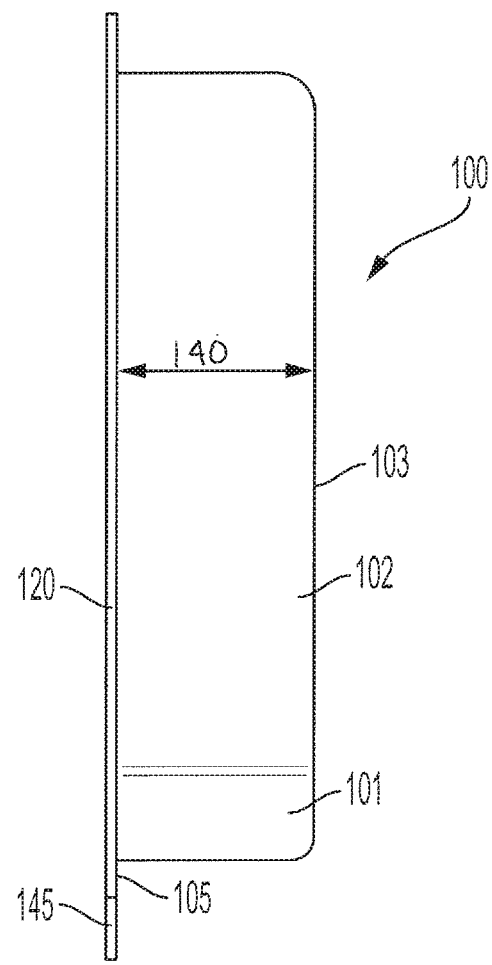
FIG. 8B shows a top elevation view of an embodiment of a cartridge, as it would be oriented when positioned in the rack. In this embodiment, an angled corner is located at the corner between the front wall and the top wall. The bottom wall can be a mirror image of the top wall, without the angled corner.

In one embodiment, cartridges 100 are positioned side-by-side, each in an orientation that has the left 6 and right side 7 perpendiculars to a horizontal surface, such as shown, for example, in FIGS. 7 and 8A. In such an embodiment, when positioned in the procedure kit 50, the side-by-side cartridges have a top edge 2 upon which the top panel 410 rests, or at least closes over, when closed, and a front edge 4 against which the front panel 440 rests, or at least closes over, when closed. In a further embodiment, a cartridge has a left side 6 that can be opened and a right side 7 that can be placed against a surface, such as a table, during use. Thus, when arranged in a kit, a cartridge can have a right side that faces the left side of another cartridge beside it.

One advantage of the procedure kit 50 is the options available for presenting information, such as, for example, graphics, alphanumeric labeling, color coding, or other visual cues 160, which can help make the procedure kit intuitive to use, as well as help make it easier to follow the methodical process of conducting the protocol correlated with the cartridges 100, components 700 therein, ancillary articles 500, and any waste cartridges 300. In particular embodiments, the shell 400 displays quick-reference information that relates to the proprietary protocol that corresponds to the procedure for which a particular procedure kit is configured. As shown, for example, in FIGS. 5A, 5B, 6 and 7, the inside of the top panel 410 can include information in a top-panel information-area 610. As shown, for example, in FIGS. 5A, 6 and 7, the inside of the front panel 420 can also include such quick-reference information in a front-panel information-area 640. In further embodiments, the top-panel information area and the front-panel information-area include information, graphics, alphanumeric labels, color codes or any combination thereof, that correlates with the cartridges, any ancillary articles, and any waste cartridges. In other embodiments, information, graphics, alphanumeric labeling, color coding, or other visual cues 160 can also be located on the outside of the shell of the kit, by any technique known in the art. Any information, graphics, alphanumeric labeling, color coding, or other visual cues located on the shell, panels, or any combination thereof, can be in the form of a sticker or label and/or ink, paint or other such medium applied to the surface.

In one embodiment, the plurality of cartridges 100 in a kit are arranged side-by-side to be utilized from left to right in accordance with the proprietary protocol that corresponds to the procedure for which a particular procedure kit 50 is configured. With this embodiment, a cartridge arranged in the far-left position of the kit 50 would be removed first in accordance with such proprietary protocol. That is, the cartridges are arranged in order of progressive use, such as, for example, the cartridge in the far-left position of the kit would contain the first components 700 utilized in a protocol.

A cartridge 100 can be a rigid or semi-rigid closed container that holds one or more components 700. Because there can be more than one cartridge in a procedure kit 50, the shape and size of each cartridge ideally allows for close proximity to other cartridges, so that space can be conserved, and the cartridges can be efficiently arranged. It can be beneficial for the cartridges to be supported in the procedure kit so that jostling, bouncing, bumping, and other undesirable movement and contact between the cartridges is inhibited.

In one or more embodiments, the plurality of cartridges is arranged in a rack 200 that supports the cartridges in a side-by-side arrangement. In this embodiment, the rack supports each cartridge separately, such that other cartridges in the rack maintain position upon removal of one or more other cartridges from the rack. In a further embodiment, cartridges can be configured for special purposes, such as, for example, a waste cartridge 300 for receiving waste materials to be disposed of, as described below. Also, ancillary articles 500 such as, for example, preparation mats or pads, syringe or test tube holder, or other components can be accommodated on the rack.

One advantage of a cartridges 100 is the available options for presenting information, such as, for example, graphics, alphanumeric labeling, color coding, or other visual cues, which can make it easier to understand the components in each cartridge, as well as how such components correlate with, and are used for conducting, the proprietary protocol that corresponds to the procedure for which a particular procedure kit 50 is configured. In one or more embodiments, there is a cartridge information-area 660 located on the left side 6 of a cartridge. The cartridge information-area can be used to display information that relates to the components contained in the respective cartridge. When the cartridge is positioned on a horizontal surface, the cartridge information-area would be on the top end 2 of the cartridge and facing upwards. In a particular embodiment, the cartridge information-area would be on the lid 120 of the cartridge, as will be described below.

In embodiments of a kit that contain a waste cartridge 300, such as a biohazard cartridge, the right side 7 of this special-purpose cartridge incudes a biohazard graphic 665, an example of a visual cue, visible when arranged in the rack 200, as shown, for example, in FIG. 2. When positioned on a horizontal surface, the biohazard graphic can face downward. In further embodiments, graphics, alphanumeric labeling, color coding, or other visual cues, or any combination thereof, can be located elsewhere on the cartridge and on cartridge inserts 107. Any information, graphics, alphanumeric labeling, color coding, or other visual cues located on a cartridge, cartridge tab, insert, or any combination thereof, can be in the form of a sticker or label and/or ink, paint or other such medium applied directly to the surface.

In one or more embodiments, a cartridge 100 has one or more walls 102 that form an enclosure around a bottom surface 103 located on the right side 7 of a cartridge to provide an interior space 104 with interior side surfaces 106. In a particular embodiment, the interior side surfaces are approximately perpendicular to the bottom surface and right side 7. FIGS. 8A-10 illustrate an example of such an embodiment.

Figure 10:
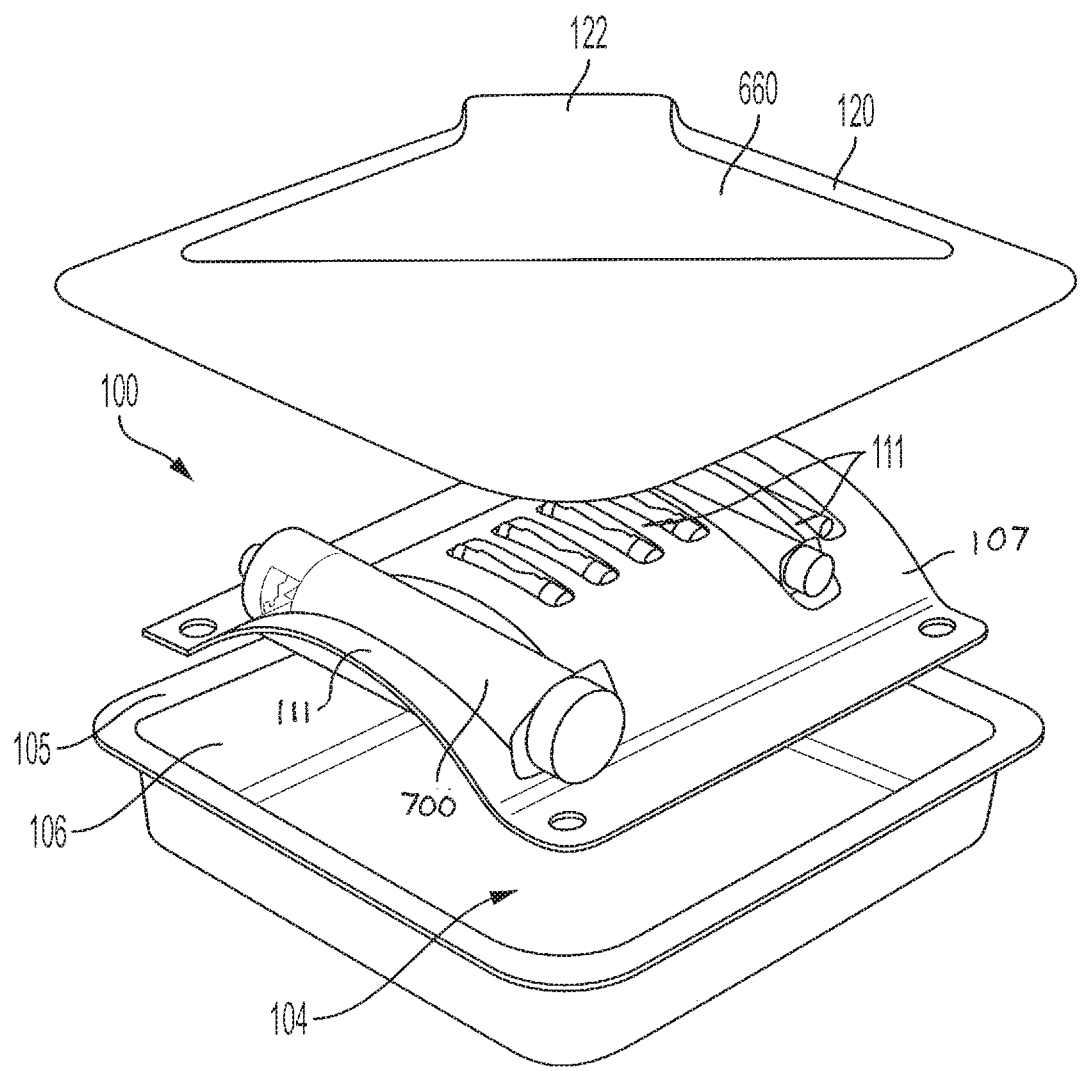
FIG. 10 is an exploded view of an embodiment of a cartridge having a lid with a tab that is labeled with information, as well as the cartridge interior space and an insert that fits into the interior space for securing components.

In one or more embodiments, components 700 are arranged in the interior space 104, such as shown, for example, in FIGS. 6 and 10. In further embodiments, the interior space has one or more inserts 107 that secure and inhibit movement of the components 700. An insert can be configured to include one or more fittings 111 that engage with, secure, and inhibit movement of individual components. FIG. 10, for example, illustrates such an insert embodiment. In yet another embodiment, there can be interior structures or fittings rising or extending from the interior bottom surface 103 and/or from one or more interior side surfaces 106 that engage with one or more components to secure and inhibit movement of the components. Such interior structures can include, but are not limited to, extensions, depressions, rises, overlays, molding, dividers, corrugations, folds, adhesives, ties, clips, pressure fittings and other configurations that components fit into, press against, slide into, are fastened down with, adhere to, or are otherwise used to secure the position of the components in the interior space.

In one embodiment, a cartridge 100 can be configured as a waste cartridge 300 for receiving waste for later disposal, such as shown, for example, in FIGS. 5A and 5B. In a further embodiment, a waste cartridge has one or more walls 102 that form a continuous, uninterrupted enclosure around a bottom surface 103 on the right side 7 that connects to a top surface on the left side 6 to form a gas and liquid impermeable interior space 104. This embodiment allows waste of a viscous nature to be transferred or deposited into the waste cartridge 300. In one embodiment, a waste cartridge includes a transfer mechanism 310, such as, for example, a luer-lock connection, slot, self-sealing film, door, or other mechanisms by which such viscous materials can be deposited into the waste cartridge. A waste cartridge with a transfer mechanism is shown, for example, in FIG. 6. Either solid or viscous waste can be a biohazard material, in which case the waste cartridge is labeled with a biohazard graphic as shown, for example, in FIGS. 2 and 4.

Cartridges 100 can have a peripheral shape that is, for example, a square, a rectangle, a parallelogram, a rhombus, a trapezoid or other four-sided shape. In one embodiment, each cartridge in a procedure kit 50 has the same peripheral shape with the same or about the same dimensions. For example, each cartridge in a procedure kit can have a quadrilateral shape with each side being at least 3", 4", 5", 6", 7", 8", 9" or 10" in length or a length in a range between any of the listed values.

In a particular embodiment, a cartridge has a square peripheral shape and includes an angled corner 101 as shown, for example, in FIGS. 8A, 8B, 9A, 9B and 9C. In a further embodiment, a cartridge has a square peripheral shape with an angled wall at a corner between a wall 102 at the front 4 of the cartridge and a wall 102 at the top 2 of the cartridge. The wall at the back 5 and bottom 3 of the cartridge do not have an angled wall and those two walls 102 that are about 6" in length.

In one or more embodiments, cartridges 100 are a thermoformed construct. In a further embodiment, an insert 107, located on the interior space 104 is a thermoformed construct. In another embodiment, a waste cartridge 300 is a thermoformed construct. Thermoform constructs can be rigid or semi-rigid and opaque, semi-opaque or translucent. In one or more embodiments, a cartridge is a semi-rigid and translucent thermoformed construct. Thermoforming materials, and the techniques and devices for forming objects from thermoform materials are known in the art and, as such, will not be discussed in detail in this disclosure. FIGS. 8A, 8B, 9A, 9B, 9C and 10, illustrates examples of cartridges that can be thermoformed constructs.

In one embodiment, there is a lid 120 that closes or seals the interior space 104. The lid can fit over all or part of the interior space and be opened or removed to provide access to the interior space. The lid can be rigid, semi-rigid or flexible, as necessary. The lid can also aid in maintaining sterility of the interior space, when sterility is applicable. Ideally, the lid is ergonomic and configured so that multiple cartridges 100 can be arranged in a rack 200 of a procedure kit 50, as described below. In a further embodiment, there is a cartridge tab 122 that is a part of the lid. In a further embodiment, the cartridge tab can extend past a cartridge flange 105, described below, and be used to remove the lid from the cartridge. Advantageously, a tab can also have thereon one or more visual cues 160 related to the cartridge. In FIG. 10, for example, the cartridge tab is an extension of a label in the cartridge information-area 660.

In one or more embodiments, a cartridge has a flange 105 that extends radially from one or more of the cartridge walls 102. In one embodiment, the cartridge flange extends radially from the left-most end of a cartridge wall, such as shown, for example, in FIGS. 8A and 8B. In a further embodiment, a flange is perpendicular to the one or more cartridge walls. The flange can provide a surface or platform to which the lid 120 can be attached. Alternatively, the flange can engage with a snap-on, slide-on, or other type of replaceable lid. In one embodiment, a flange radially extends from each interior side surface and cartridge wall as shown, by way of example, in FIGS. 9B and 9C. In a further embodiment, a flange follows or corresponds to the peripheral shape of the cartridge. Thus, for example, a flange could also have an angled edge 145 that corresponds to and angled wall 101, as illustrated in the example in FIG. 9B. In an alternative embodiment, the flange is incomplete, in that, there is at least one interior side-surface and cartridge wall, or some portion thereof, from which the flange does not radially extend.

A flange can radially extend from a side wall by a distance of at least 0.1 in., 0.2 in., 0.3 in., 0.4 in., 0.5 in., 0.6 in., 0.7 in., 0.8 in., 0.9 in., 1.0 in., 1.1 in., 1.2 in., 1.3 in., 1.4 in., 1.5 in. or a distance in a range between any of the listed values. As described above, a cartridge can have a peripheral shape with each side being at least 3", 4", 5", 6", 7", 8", 9" or 10" in length or a length in a range between or above any of the listed values. For a cartridge that includes a flange on one or more sides, the length of the flange is at least 3", 4", 5", 6", 7", 8", 9" or 10" in length or has a length in a range between any of the listed values.

Figure 9A:
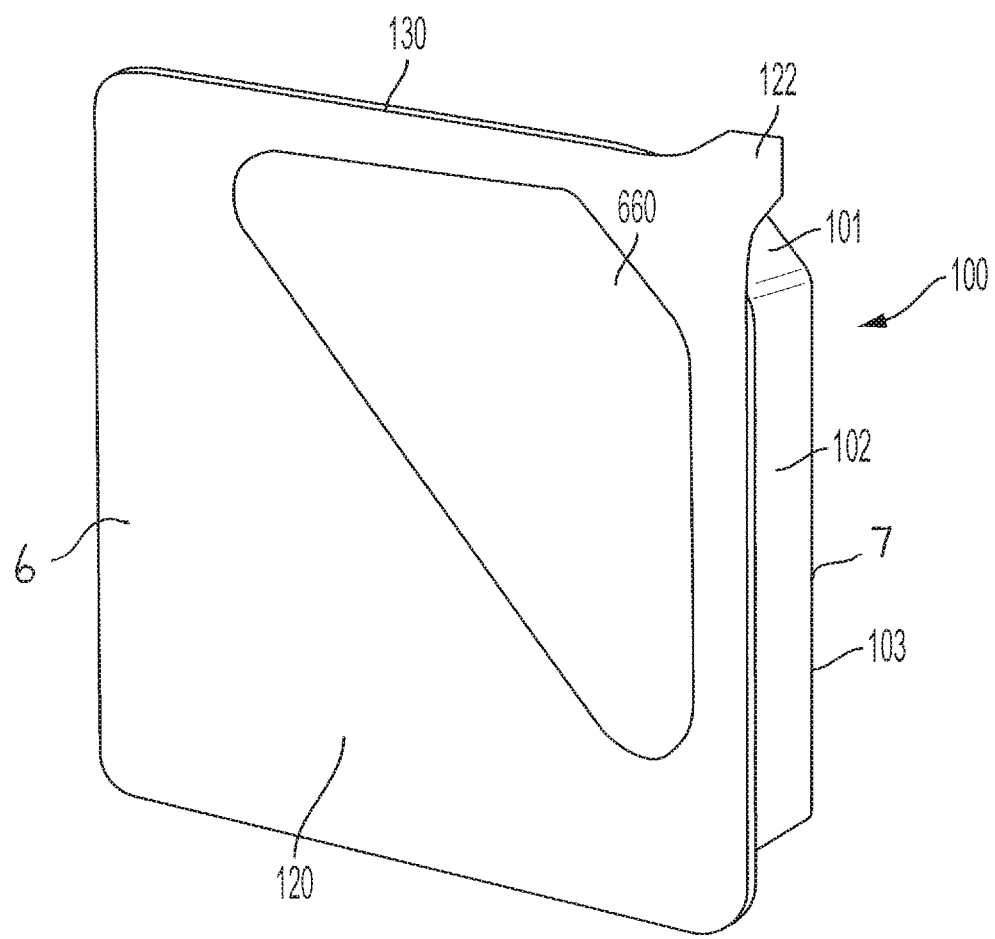
FIG. 9A shows a top and left-side perspective view of one embodiment of a cartridge with a rigid or semi-rigid lid.
Figure 9B:
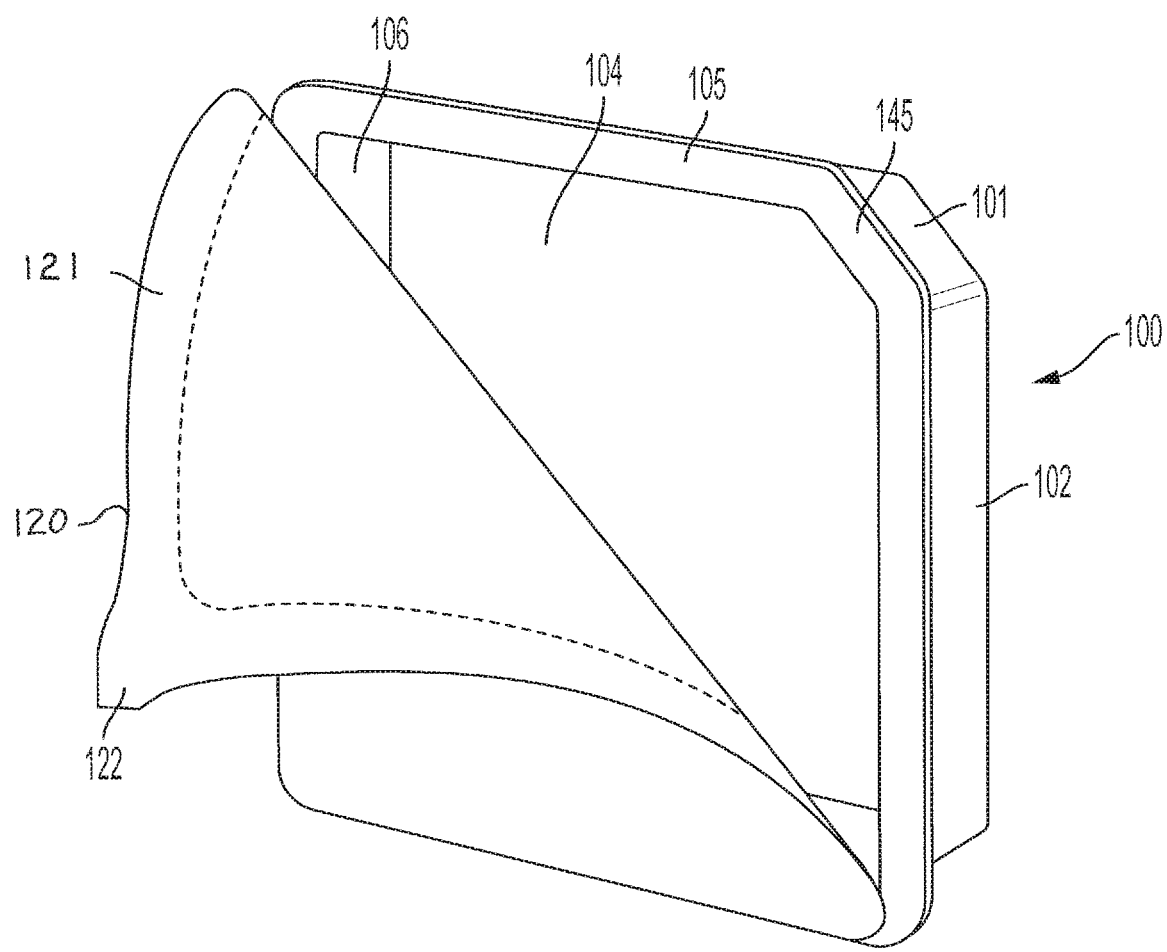
FIG. 9B shows a top and left-side-perspective view of an embodiment of a cartridge with a lid that can be peeled off the flange of the cartridge to access the components in the interior space.
Figure 9C:
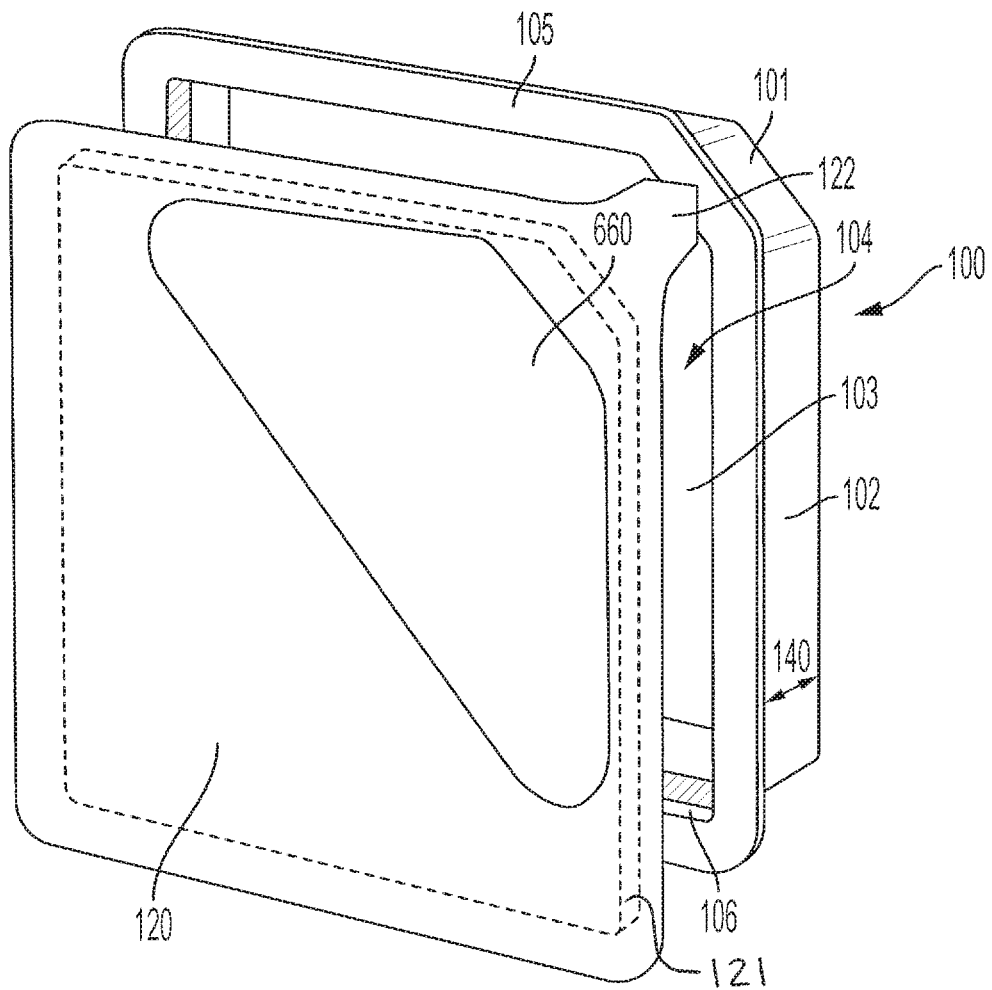
FIG. 9C shows a top-perspective view of another embodiment of a cartridge with a lid that has a lip on an inside surface that extends into the interior space and engages with the interior side surfaces.
Figure 9D:
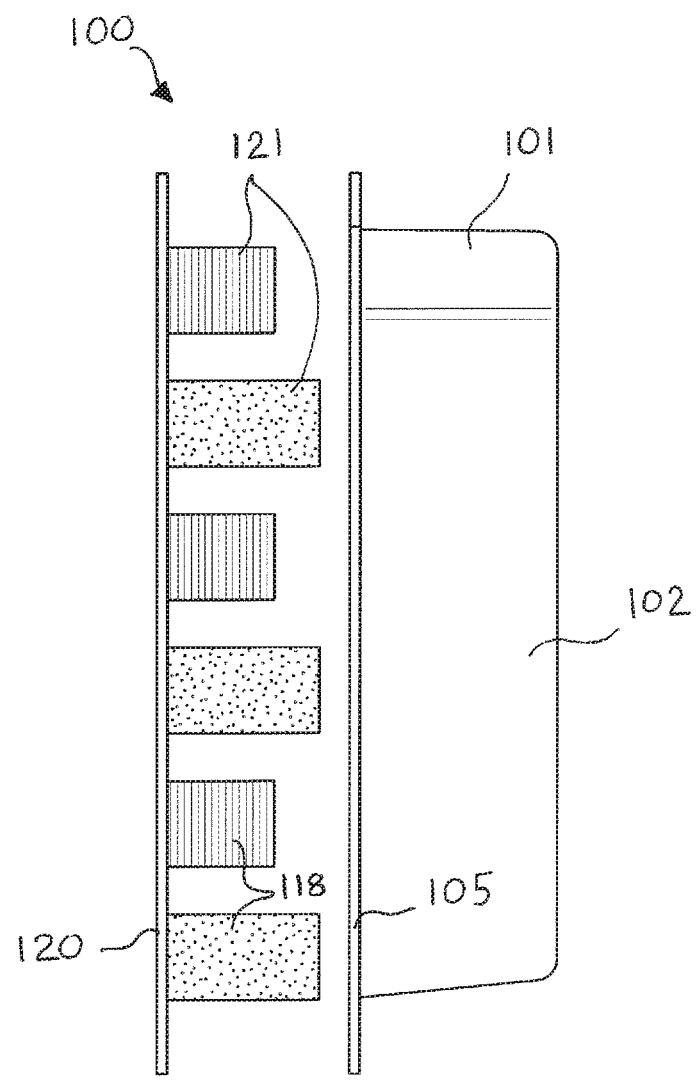
FIG. 9D shows an exploded front elevation view of the cartridge embodiment shown in FIG. 9C.

In one or more embodiments, the lid 120 of a cartridge 100 is removable and replaceable. For example, the lid can be configured to engage with the flange 105, so that it can be removed and reengaged to reclose the interior space 104. In one embodiment, the flange and/or the lid can have a reusable adhesive thereon that allows the lid to be peeled or pulled off the flange and reattached. In other embodiments, the lid can snap onto the flange so that it can be removed and then be snapped back onto the flange again to reclose the interior space. In another embodiment, the lid can have one or more lips 121, one non-limiting example of which is shown in FIGS. 9C and 9D, which extend out or away from the bottom end 3 of the lid to engage with one or more of the interior side surfaces 106. The lid with the lip thereon can be removed from, and reengaged with, one or more of the wall 102 interior side surfaces to open and then reclose the interior space.

In one embodiment, the one or more lips can form a friction fit with the interior side surfaces of the one or more walls. FIGS. 9C and 9D illustrate non-limiting examples of a lid with a lip or lips. FIG. 9C illustrates an example of one lip formed on the bottom end of a lid that circumscribes periphery of and friction fit with the interior side surfaces. FIG. 9D illustrates an example of multiple lips of different sizes formed on the bottom end of a lid that form a friction fit with sections of the interior side surfaces. With these embodiments, the lid can be peeled or pulled from the cartridge to disengage a lip from the interior side wall. The lid can be realigned with the interior side walls and pushed to reengage the lip with the side walls. The one or more lips can have any of a variety of configurations capable of engaging with the interior side surfaces. A lip can also have one or more surface features 118 that enhance or facilitate engagement with the interior side wall 106, such as, for example, rough textures, dimples, ridges or areas of increased stiction. In other embodiments, the lid is configured to engage with one or more of the interior side surfaces 106 and/or flange 105, so as to be all or partially removable to access the interior space, but does not reengage or fully reengage with the interior side surfaces and/or flange of the cartridge to reseal the cartridge after being partially or fully removed. Such variations that perform substantially the same function, in substantially the same way, with substantially the same result are within the scope of this invention.

In one or more other embodiments, the lid 120 can be fixedly attached to the cartridge 100. In a further embodiment, the attached lid is folded over, flipped-up, rotated, raised, or otherwise displaced on the cartridge to access the interior space 104, without being entirely removed from the cartridge. For example, the cartridge and lid can have a clam-shell configuration, which allows the lid to be flipped or rotated along one edge of the cartridge.

In one or more embodiments, a lid 120 can be a pliable or a film-like material that is adhered to, heat sealed, crimped, shrink-wrapped, or otherwise attached to the flange to initially close or seal the interior space. Films or other covering materials are commonly used to seal containers. In a further embodiment, lids made of such films or other covering materials can be resealed because of a reusable material, such as a reusable adhesive described above, that is applied to the lid, and/or the top end 2 of the flange, so that the lid can be reattached to the surface of the flange. A lid made of such film or other covering materials is shown, for example, in FIG. 9B.

Different procedures can require different components 700 for each step of the protocol specific to each particular procedure kit 50. As such, each cartridge 100 in a procedure kit can contain different quantities, types and sizes of components depending upon the specifications of the protocol required to perform a particular procedure. Where the cartridges in a procedure kit have the same or about the same peripheral shape and dimensions, the cartridge depth 140, (distance in the interior space 104 between a lid 120 and the bottom surface 103) can be variable so that the interior space 104 can be made to accommodate different sizes of components. In one or more embodiments, the cartridge depth varies in discrete increments. For example, cartridges can have a minimum depth of 0.5", 1", 1.5", 2" or 2.5" or a depth in a range between or above any two of the listed values. In further embodiments, cartridges can have depths that are multiples of the minimum depth of a cartridge. For example, if 0.75" is the minimum depth for a cartridge, larger or deeper cartridges can have depths that are multiples (2×, 3×, 4×, etc.) of that minimum depth, such that cartridges would have depths of, for example, 1.5", 2.25", 3", etc. FIG. 5B illustrates an example of a 1× and 2× cartridge depth.

While it is possible for a procedure kit 50 to include one cartridge 100, it is more likely that a procedure kit will have a plurality of cartridges. The number of cartridges, ancillary articles 500, and waste cartridges 300 in a particular procedure kit will, however, depend upon the type of procedure for which the procedure kit has been configured. The protocol for a procedure that calls for a large number of cartridges can require a procedure kit that is wider between the left end 6 and the right end 7.

In one or more embodiments, cartridges 100 fit into the rack 200 and the rack has a slot 225 into which a flange 105 of a cartridge can be inserted to secure the cartridge. With this embodiment, there is minimal or no contact between cartridges when placed in the rack and the rack can support a plurality of cartridges arranged side-by-side as illustrated, for example, in FIGS. 5A, 5B, 6, and 7. With this embodiment, each flange is pushed into and pulled out of its own slot and cartridges are individually supported by the rack. In addition, the rack can provide the cartridge with further stability because one wall 102 of the cartridge can sit on one or more landings 215 of a rack seat 230, and an adjacent wall of the cartridge can rest against one or more landings of a rack back 220, as shown in FIGS. 5A, 5B, 6 and 7. With this embodiment, the rack has a "L-shape," as shown in the examples in FIGS. 11A and 11B.

In one embodiment, when a flange 105 is fully engaged with a slot 225, as shown in FIGS. 5A, 5B, 6, and 7, the slot is continuous from the top of the rack back 220 to the front of the rack seat 230, which secures the cartridge in an upright, vertical orientation. In a further embodiment, where the slot contacts a flange, the slot has a friction fit with the edges of the flange. In one embodiment, where the slot contacts the flange, the slot has a width of about 0.1", 0.2", 0.3", 0.4", 0.5" or width between any of the two listed values.

Ancillary articles 500 and waste cartridges 300 can also include flanges 105 or similar elements that can be inserted into one or more slots 225. Ancillary articles and waste cartridges can also be configured similar to a cartridge, so as to include surfaces that rest on one or more landings 215 of a rack seat 230, and/or rest against one or more landings of a rack back 220, when arranged in a procedure kit 50. FIGS. 5A and 5B illustrate, for example, a top view and front elevation view, respectively, of an ancillary article and waste cartridge arranged in the rack 200. FIG. 6 illustrates, for example, an ancillary article removed from the rack and set up for use with components 700 removed from a cartridge 100, and a waste cartridge that remains in the rack.

Figure 11A:
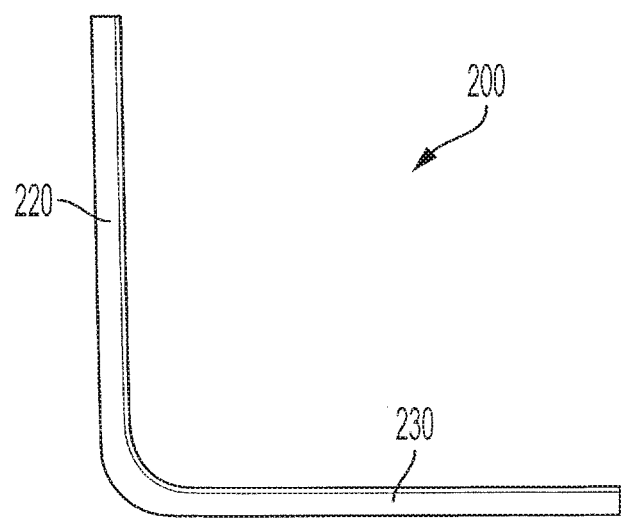
FIG. 11A shows the left-side elevation view of one embodiment of a rack, as it would be oriented if viewed from the left side of a procedure kit.
Figure 11B:
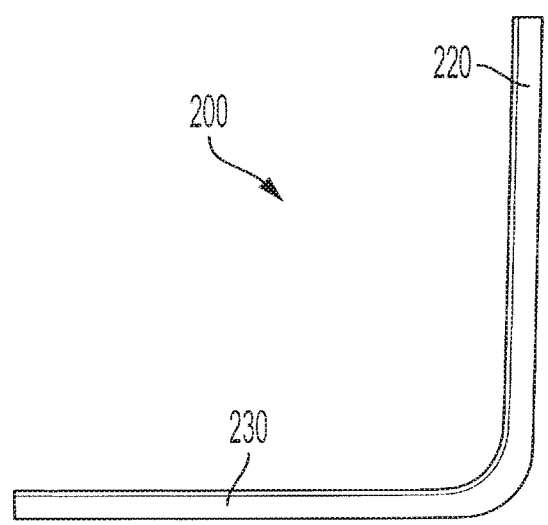
FIG. 11B shows the right-side elevation view of one embodiment of a rack, as it would be oriented if viewed from the right side of a procedure kit.

In one embodiment, an L-shaped rack, as illustrated, for example, in FIGS. 11A and 11B, has one or more evenly spaced slot-and-landing pairs 210. The slot-and-landing pairs can extend from the top 2 of the rack back 220, downward to where the rack back meets the rack seat 230, and then out to the front 4 of the rack seat. This provides slot-and-landings pairs that are continuous and unobstructed as illustrated, for example, in FIGS. 12A, 12B, 12C and 13. Accordingly, each L-shaped slot 225 of the rack can secure flanges on both the back end and bottom end of a cartridge when placed in the rack with the flange engaged with the slot. Further, each L-shaped landing 215 can provide a place for a back cartridge wall 102 to rest and a bottom cartridge wall to sit.

Thus, there can be a relationship between the plurality of cartridges 100 and the rack 200 in which the cartridges are arranged. Specifically, the rack can be configured to support a plurality of cartridges having particular dimensions and shapes. While cartridges and the rack therefor are not limited in the shape or dimensions, it can be beneficial for the rack and cartridges to have consistent or standardized dimensions and shapes. It can be further beneficial for these dimensions and shapes to be of a modular nature, such that the rack and cartridges relate to each other and can be interconnected and rearranged as necessary for any particular procedure kit. This uniformity and similarity of configuration can further facilitate familiarity with the basic design of procedure kits 50, so that there can be an intuitive understanding of different types of procedure kits. Thus, the modularity of the procedure kit provides standardization that can make it easier for users to perform a variety of different procedures, even though each particular procedure kit may require different numbers of cartridges with different types, sizes and quantities of components 700.

In one or more embodiments, one or more cartridges 100 have a similar peripheral shape and dimensions, but different cartridge depths 140. In such embodiments, the rack 200 can be configured to support the one or more cartridges with similar peripheral shapes and dimensions but having different cartridge depths. The slot-and-landing pairs 210 of any rack of the subject invention can have a width 150 equivalent to or approximately equivalent to the smallest cartridge depth, and cartridges can have depths that are multiples (e.g., 2X, 3X, etc.) of the smallest cartridge depth, which can span, for example, two or more slot-and-landing pairs. FIGS. 5A and 5B illustrate an example of two cartridges, each with a 2× cartridge depth, that span two slot-and-landing pairs each. The modularity of the design is, in part, what provides for standardization of the disclosed invention while, at the same time, allowing a variety of types of procedures kits to be configured.

In one embodiment, a rack 200 is a single length of material with a series of one or more slot-and-landing pairs 210. By way of a non-limiting example, a rack can be extruded to a width with the required number of slot-and-landing pairs for a particular procedure kit. In a further embodiment, a rack has an edge detail 235 at both the left 6 and right 7 ends of the rack, such as illustrated, for example in FIG. 12A. The edge details can be utilized to join two or more racks into a longer rack with more slots-and-landing pairs. Thus, each rack becomes a rack segment 205. For example, the rack 200 shown in FIG. 12A, which has eight slot-and-landing pairs and edge details 235 at both the left side 6 and the right side 7, can be used as a rack segment 205 and joined with the edge details to form a rack with 16 slot-and-landing pairs. This can provide further modularity to the procedure kit to accommodate different sizes of kits.

Figure 12A:
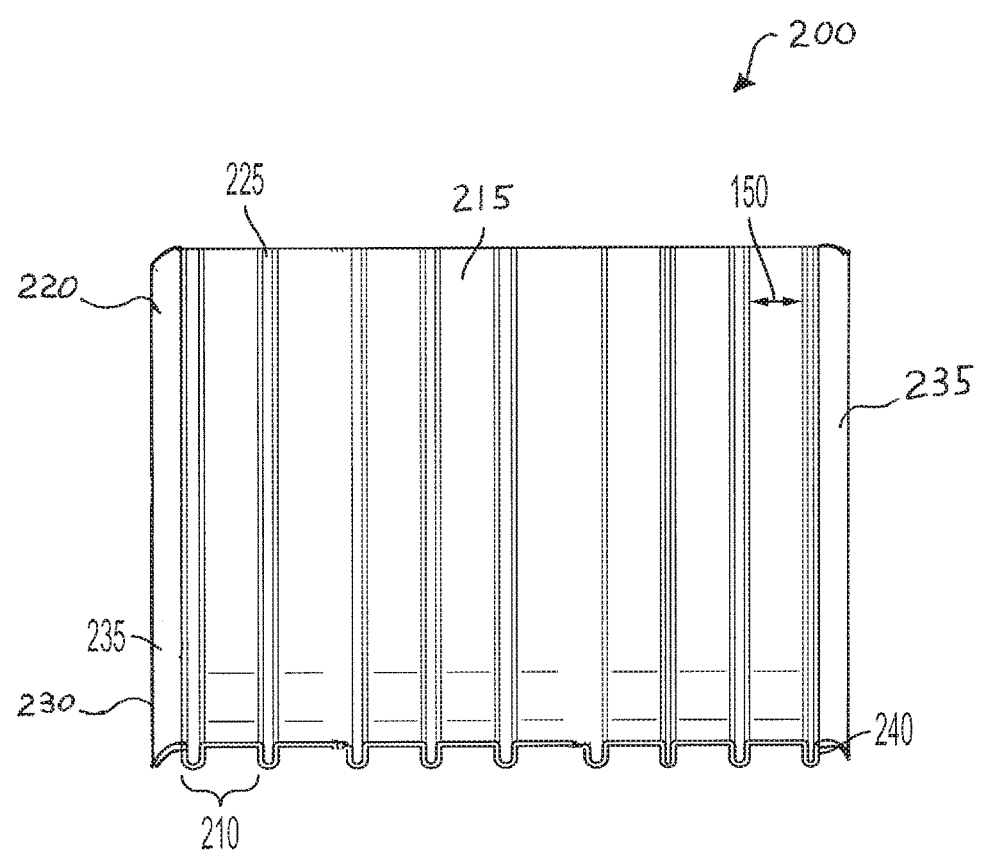
FIG. 12A shows the front view of an embodiment of a rack, which has a required number of slots and landings for a particular procedure kit.
Figure 12B:
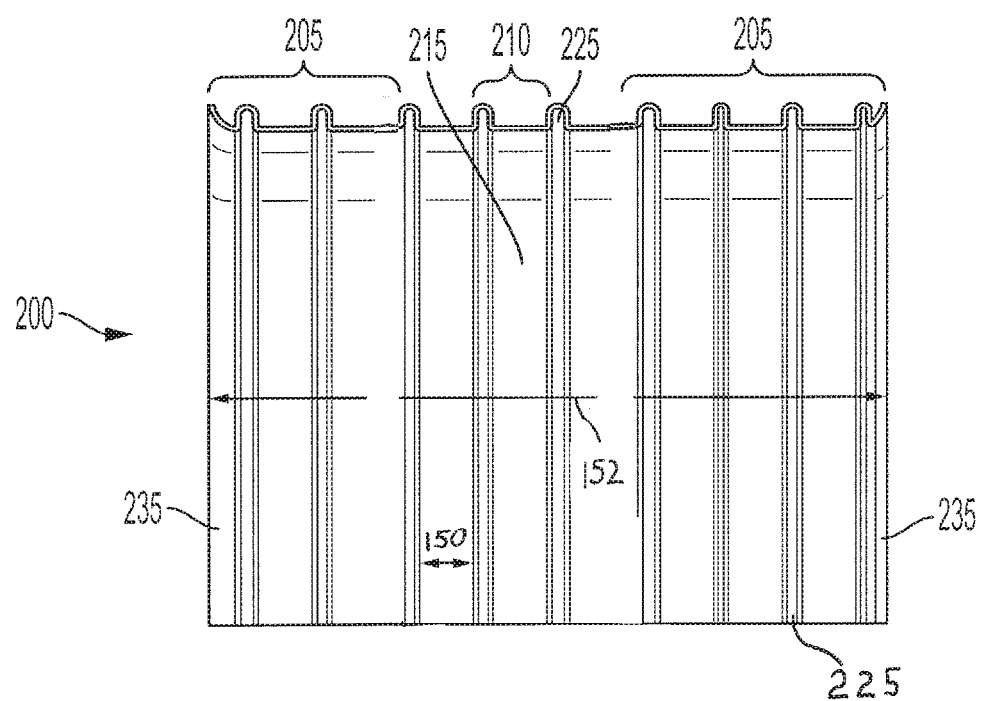
FIG. 12B shows the top view of an embodiment of a rack, which comprises three rack segments joined together by the edge details on each side.

Different procedure kits can require different numbers of cartridges, ancillary components, and/or a waste cartridge. Thus, it may be necessary for a rack to have fewer than eight or less than sixteen slots-and-landing pairs 210. To provide more precise modularity that accommodates this variability in procedure kits, a rack segment can have any number of slot-and-landing pairs, can be of the same or a different number of slot-and-landing pairs, and can have an edge detail at both the left and right ends of the rack segment. In further embodiments, the edge detail at the right side of one rack segment can be connected to the left side edge detail of another rack segment, as described above, to extend the left-to-right width 152 dimension of the rack. FIG. 12B illustrate an example of a rack composed of three rack segments 205, where the left-most 6 rack segment has two slot-and landing pairs and the two other rack segments that each have three slot-and-landing pairs, providing a rack with eight total slot-and-landing pairs. Rack segments are not limited to two or three slot-and-landing pairs and could have any number of slot-and landing pairs. Thus, additional rack segments could be joined to the rack shown in FIG. 12B to compose a rack with more slot-and-landing pairs, or different combinations of rack segments with different numbers of slot-and-landing pairs could be joined to compose a rack of any number of slot-and-landing pairs.

Figure 12C:
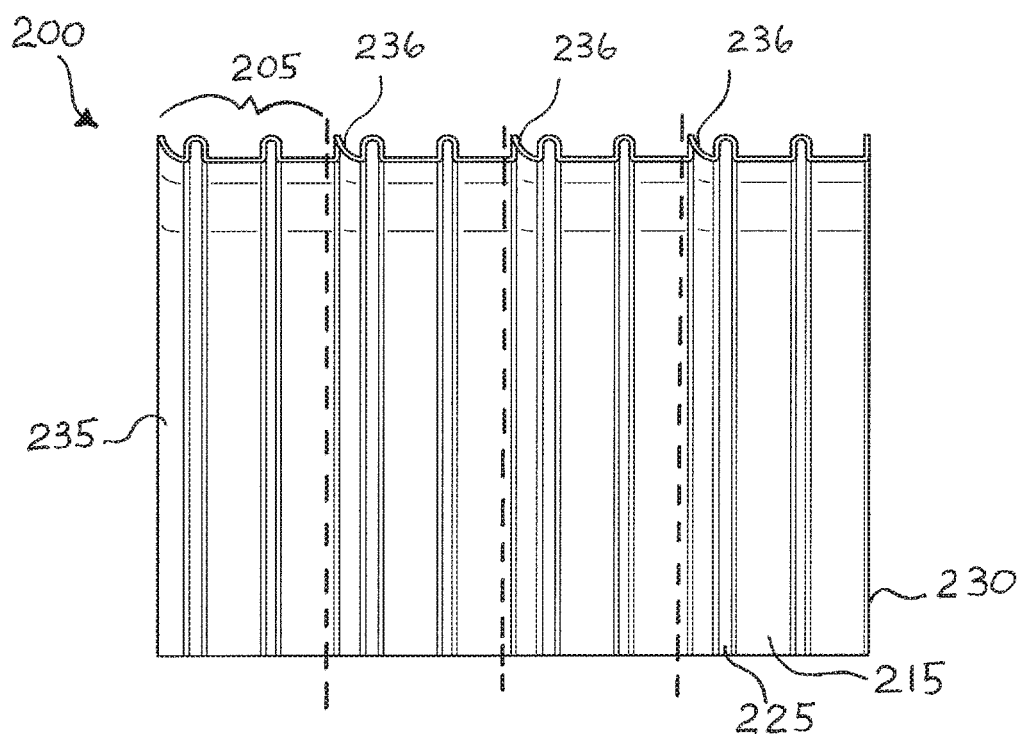
FIG. 12C shows the top view of an embodiment of a rack element with both edge details and intermediary details. The dashed lines indicate where the rack element can be cut to provide individual rack segments that can be joined to other rack segments to form a rack of any width and numbers of slot-and-landing pairs.

In a particular embodiment, multiple rack segments 205 can be formed as a rack element 250. The rack element can be separated, cut, broken, or otherwise divided into multiple, separate rack segments. By way of a non-limiting example, a rack element can be formed by an extrusion process. The extruded rack element can then be divided at specific points to provide two or more rack segments. In one embodiment, the rack element is formed with edge details 235 and intermediary details 236, such that when the rack element is divided, the individual rack segments have edge details that allow them to be rejoined. The divided rack segments can have any number of slot-and-landing pairs, allowing the rack segments to be rejoined to form a rack with the necessary number of slot-and-landing pairs for a particular procedure kit 50. FIG. 12C illustrates an example of a rack element 250 that can be divided to form four rack segments, with two slot-and-landing pairs 210 each. The dashed lines on FIG. 12C indicate lines along which the rack element can be divided, preferably adjacent to an intermediary detail, such that the resulting rack segments each have a left side 6 and right side 7 edge detail that can be used to rejoin the rack segments from that or another rack element to form a larger rack.

Figure 13:
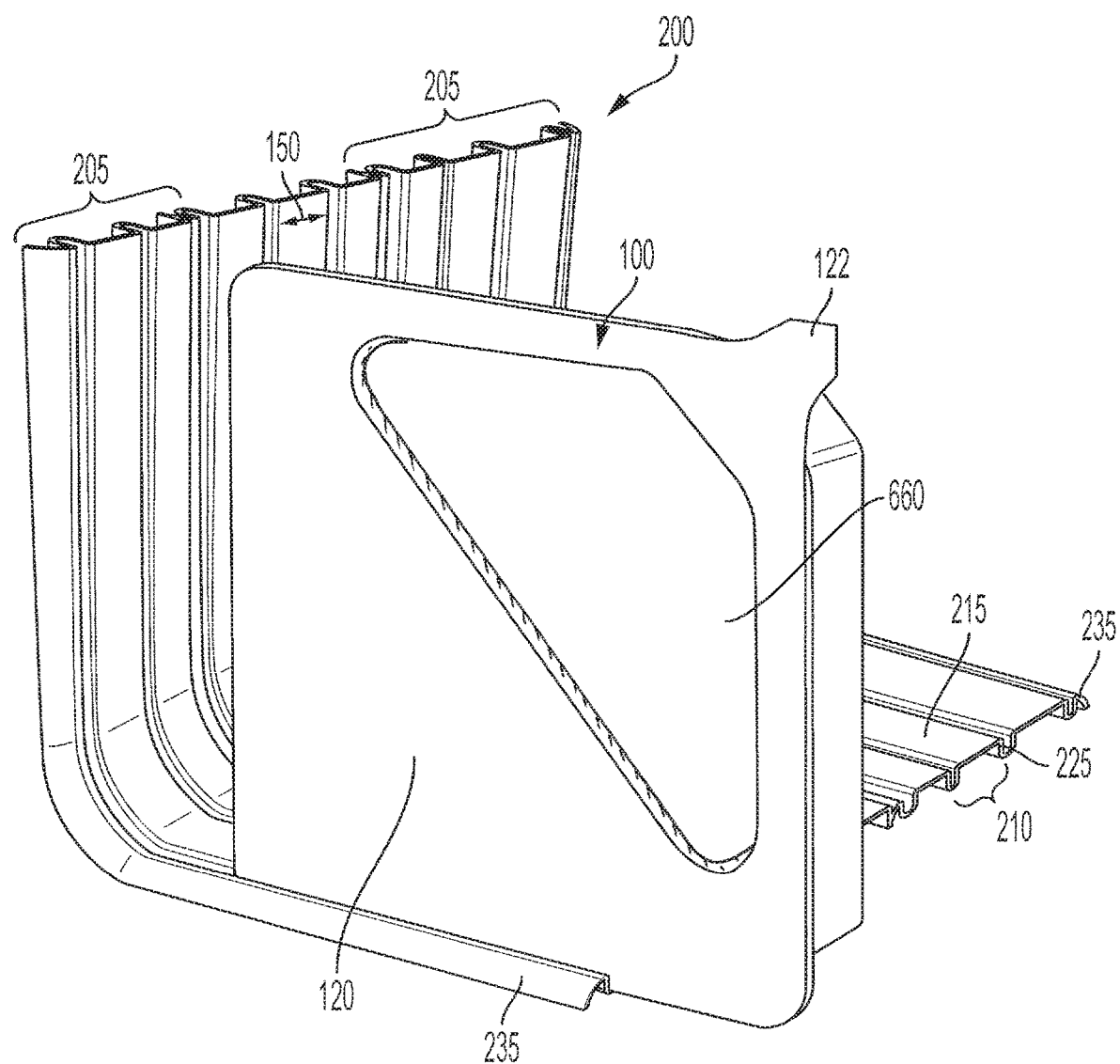
FIG. 13 shows a left-side-perspective view of an embodiment of a rack with a cartridge partially slid forward on the rack seat and away from the rack back.
Figure 14:
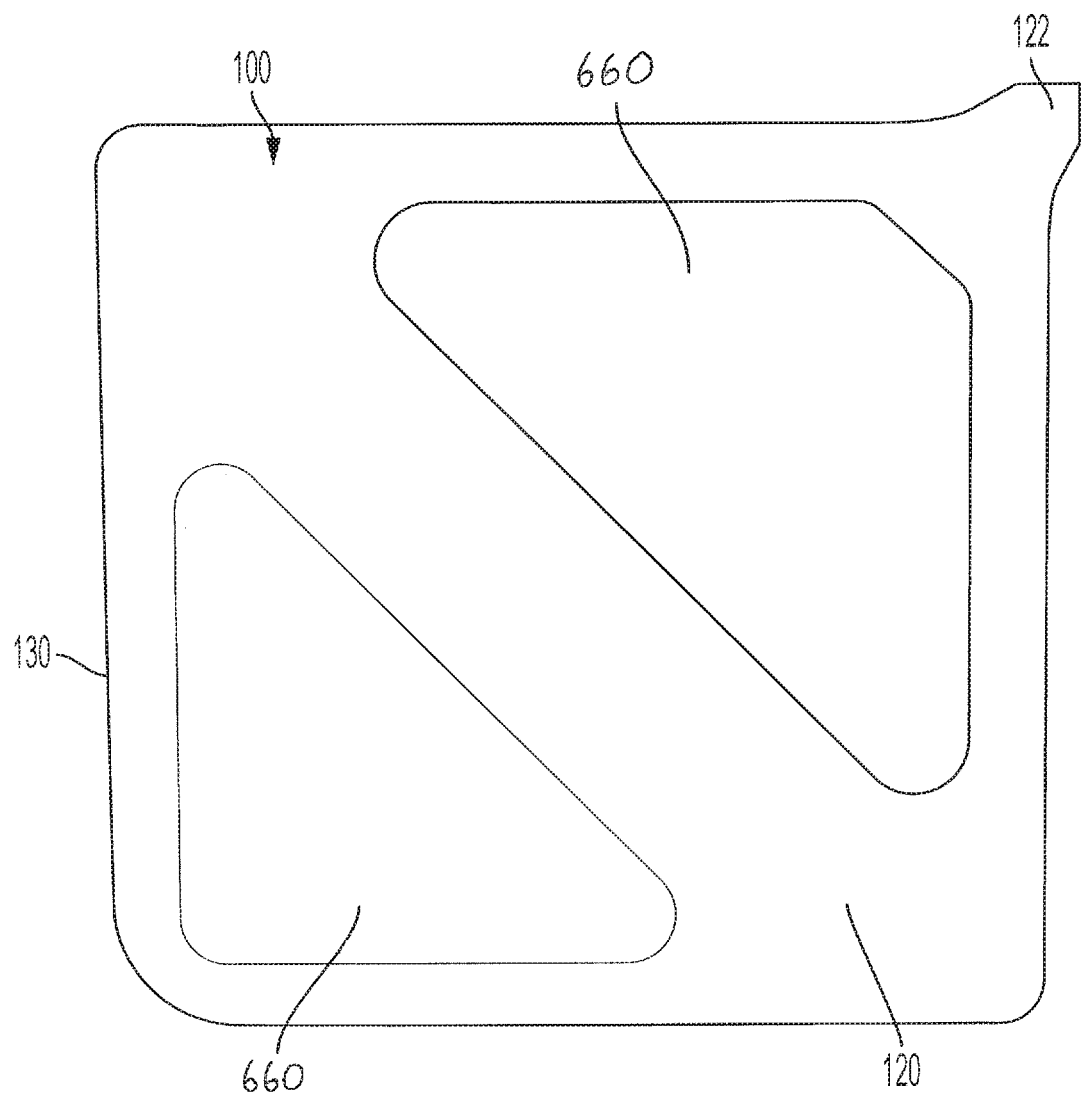
FIG. 14 is a left side elevation view of an embodiment of a cartridge with a lid.

In embodiments where rack segments 205 are joined together to extend the rack width, edge details 235 can be connected by several techniques including, but not limited to, welding, adhering, clipping, fitting, interdigitating, overlapping, crimping, or other techniques, known to those with skill in the art. In a further embodiment, the edge details can be configured to connect and form a friction fit to lock them together by clicking, snapping, pressing, or otherwise fitting one edge segment into or over another. FIGS. 12B and 13, for example, illustrate three rack segments connected to form a rack 200, with eight slot-and-landing pairs 210. Depending upon the type of procedure for which a procedure kit 50 is configured, there can be any number of slot-and-landing pairs. Further, depending upon the number of slot-and-landing pairs in each rack segment, two or more rack segments can be connected to create rack with the appropriate number of slot-and-landing pairs.

In one embodiment, a rack segment is cut from an extruded material, which has any even number of slot-and-landing pairs. In this embodiment, the extruded material has an edge detail 235 at both the left and right ends of the extruded material. In a further embodiment, there is also an intermediary edge detail 236 located between every two sets of slot-and-landing pairs of an extruded rack. An intermediary detail can be substantially similar to a slot 225 and can, when cut or otherwise split, form an edge detail for the adjacent rack segments 205 to the right and left which are thereby separated. The intermediary details allow a rack or rack segment of a desired width 152 to be cut from the extruded rack material, such that an intermediary detail can then become an edge detail. For example, material can be extruded to form two or more rack segments. The combined, extruded rack segment can then be cut for form two or more racks or rack segments, with the intermediary edge details becoming edge details after the cut. FIG. 12C illustrates an example of such an extruded material.

Example 1: Method of Using a Procedure Kit for the Performance of a Medical Treatment A procedure kit contains three cartridges arranged in the first three positions at the left side of a rack, an ancillary article, which is a vial holder, is arranged in the rack to the right of the cartridges, and a waste cartridge, which can contain biohazard material, is arranged at the furthest most right-side of the rack. The biohazard cartridge includes a lure-lock connection, which is the means by which syringes contained in the procedure kit transfer viscous biohazard materials into the biohazard cartridge. The procedure kit has been wrapped in a sterile barrier and sterilized after the closure of the shell of the kit with the contents inside.

To be used in a sterile field, the procedure kit would be carried into the area where the procedure is to be performed. The sterile barrier, which encloses the procedure kit, would be opened and the procedure kit removed from inside the sterile barrier, in accordance with sterility standards recognized in the art to preserve the sterility of the procedure kit. The sterile procedure kit can then be placed in the sterile field.

The procedure kit would be opened by removing the unseal strip from the unseal flap, which overlays the reseal flap there beneath. After removal of the unseal strip, the unseal flap is lifted from the reseal flap. Once the unseal flap has been lifted, the top panel would be lifted and rotated up and backward to provide access to the top of the cartridges and to reveal quick-reference information that is provided on the inside surface of the top panel. Likewise, the front panel would be pulled down and forward to lay down in front of the kit, thereby providing access to the front of the cartridges and revealing quick-reference information that is provided on the inside surface of the front panel. The quick-reference information on both the top and front panels provides a general sense of the organization and contents of the procedure kit, and abbreviated information pertaining to the step-by-step instructions of the protocol with which the cartridges, components, ancillary article and waste cartridge correlate.

Once the shell of the kit is opened, the arrangement of the cartridges, ancillary articles, and waste cartridge will provide the user with a sense of the organization of, and the methodology of using, the procedure kit. The cartridges in the kit have tabs printed with sequential numbers. The tabs are used to open each respective lid and the numbers on the tabs provide the user with a sense of the orderly process for using the procedure kit. Each cartridge also has information in the upper-right area of the lid, which provides additional information that relates to the components in each respective cartridge. The bottom-left area of each lid is clear, which provides an opportunity to view the contents of each respective cartridge.

The first cartridge, which is located at the left of the rack, would be removed by pulling it up and outward. The cartridge would then be opened by using the cartridge tab to remove the lid. The components therein would then be used to conduct all or a portion of the first step of the proprietary protocol with which the components correlate. Once the components are used or no longer needed, they are returned to the cartridge, the lid is replaced, and the cartridge is returned to the same location in the rack, which, in the case of this first cartridge would be at the left-most end of the rack. Once the first cartridge is returned to the rack, the user can be assured that all the components in it have been used and accounted for.

The second cartridge, which is located to the immediate right of the first cartridge in the rack, would next be removed by pulling it upward and outward and then opened in the same manner as the first cartridge. The information provided on the lid directs the user to remove the ancillary article, which, in this example, is a syringe holder, and to set it up in the sterile field. The second cartridge contains two syringes prefilled with anticoagulant, a butterfly needle, a tourniquet, gauze, and an adhesive bandage. The components in the second cartridge have been organized to complete the next steps of the protocol, which requires obtaining blood from the patient. After blood has been drawn into the first syringe, the luer-lock connector on the butterfly needle would be removed from the luer-lock connector of the first syringe, and the first syringe would be placed into the syringe holder. The process of drawing blood from the patient would then be repeated with the second syringe.

The third cartridge, which is located to the immediate right of the second cartridge in the rack, would next be removed by pulling it upward and outward and then opened in the same manner as the first and second cartridges. The components in the third cartridge include transfer hubs and preparation syringes. These components would be used with the blood-filled syringes of the second cartridge. Accordingly, the blood from each syringe of the second cartridge would be transferred into each preparation syringe, respectively, to prepare the patient's blood for therapeutic use in accordance with the next steps of the protocol. Once the next steps of the protocol have been completed, the prepared blood in the lower portion of the preparation syringes would be transferred back into the syringes from the second cartridge, and the waste from the preparation syringes would be transferred into the waste cartridge, which is a biohazard container, via the luer-lock port. The waste cartridge can be, but does not have to be, removed from the kit for use. Then, the prepared blood would be used to treat the patient. Once completed, the components from the second and third cartridges would be returned to their respective cartridges, and the respective lids would be replaced, then the second and the third cartridges would be returned their respective positions in the rack. Next, the ancillary article, i.e., the syringe holder, would be returned to its original position in the rack and the biohazard cartridge, if necessary, would be returned to the far-right position in rack. Alternatively, depending upon disposal rules and regulations to which the user is subject, the biohazard cartridge, any other cartridge, component, ancillary article, or any combination thereof, could be disposed of separately.

Once all of the cartridges, with the components therein, have been returned to the rack, in accordance with rules and regulations to which the user is subject, the top panel and the front panel would be rotated back to their original, closed positions over the cartridges, with the reseal flap secured on top of the unseal flap. The protective cover on the adhesive strip located on the reseal flap would be removed, so that the reseal flap would adhere to the unseal flap. Once the shell of the kit has been resealed, the procedure kit and the contents would be disposed of in accordance with rules and regulations to which the user is subject.

As evidenced in the example above, the preparation of a medical treatment in the field of regenerative medicine is performed as a series of steps that utilize components at each step. While the preparation of such treatments must adhere to certain general standards, they are not always performed with the same steps, in the same order of steps, with the same components, or using the same techniques. The procedure kits of the subject invention provide the advantage of being configurable for the specific procedure or treatment that needs to be prepared for each specific patient need. Further, each configuration of a procedure kit of the subject invention provides for a consistent methodology of conducting a proprietary protocol for the preparation of each particular treatment. In addition, each procedure kit provides the components necessary to efficiently and precisely prepare each particular treatment in accordance with the included proprietary protocol with which the components correlate. Such a standardization system and methodical approach can accelerate the rate at which new medical treatments are adopted and can make it possible for a variety of people in different locations to efficiently and precisely prepare medical treatments with consistent and effective outcomes. In addition, the efficient preparation of medical treatments can reduce wasted time and materials which, thereby, can reduce costs; and, the precise preparation of medical treatments can reduce the chance of errors which, thereby, can decrease patient risk.

The examples above, and embodiments described herein, are for illustrative purposes only. Various modifications or changes in light thereof are to be included within the spirit and purview of this application.

Any reference in this disclosure to "embodiment," "one or more embodiments," "further embodiments," "other embodiments," etc., is for literary convenience. The implication is that any feature, element, or characteristic described in connection with such an embodiment is included in at least one embodiment of the invention. The appearance of such phrases in various places in this disclosure does not necessarily refer to the same embodiment. In addition, any aspects or limitations of any invention or embodiment thereof disclosed herein can be combined with any and/or all other aspects or limitations, individually or in any combination. or any other invention or embodiment thereof disclosed herein, and all such combinations are contemplated with the scope of the disclosed invention without limitation thereto.

What is claimed is:

1. A single-use procedure kit, configured for the methodical performance of the steps of a procedure, comprising:
   a shell that defines a storage compartment comprising a top panel, a bottom panel, a front panel, and a back panel, and an unseal flap between the top panel and the front panel that is displaced with the top panel when the storage compartment is unsealed to provide access to the storage compartment;
   a rack comprising a rack back, a rack seat, and at least one slot and at least one landing, providing at least one slot-and-landing pair that is continuous across the rack back to a front of the rack seat, the rack being fixedly arranged against the back panel and the bottom panel within the storage compartment;

one or more cartridges, each cartridge comprising at least one wall and a bottom surface that define an interior space having a depth configured to contain at least one component used to perform a step of the procedure, an at least partially removable cover that closes the interior space, a flange that slidably engages with the at least one slot of one of the at least one slot-and-landing pair, so that the at least one wall is supported on the at least one landing of the rack back and the rack seat, such that, when the top panel is displaced with the unseal flap, the one or more cartridges are removable in an order corresponding to the steps of the procedure.

2. The procedure kit, according to claim 1, further comprising the front panel being displaced forward when the unseal flap is unsealed, to provide front access to the storage compartment and the rack seat.

3. The procedure kit, according to claim 1, wherein the at least one component in the one or more cartridges is utilized to perform a step of the procedure.

4. The procedure kit, according to claim 1, further comprising a slot-and-landing pair at a left side of the rack and a slot-and-landing pair at a right side of the rack, such that a cartridge with a flange slidably engaged with the slot-and-landing pair on the left side and a cartridge with a flange slidably engaged with the slot-and-landing pair on the right side form a left sidewall and right sidewall, respectively, such that the storage compartment is enclosed when the unseal flap is positioned between the top panel and the front panel.

5. The procedure kit, according to claim 4, further comprising at least one edge detail on the rack for connecting two or more racks.

6. The procedure kit, according to claim 1, wherein the at least partially removable cover is replaceable on the cartridge to reclose the interior space.

7. The procedure kit, according to claim 1, further comprising at least one lip on the at least partially removable cover, the lip being engageable with an interior side surface of the cartridge.

8. The procedure kit, according to claim 6, wherein the at least partially removable cover is a lidding film.

9. The procedure kit, according to claim 1, further comprising one or more cartridge having a depth that is a multiple of the depth of another cartridge, such that at least one wall overlaps at least one slot-and-landing pair to be supported by at least two landings.

10. The procedure kit, according to claim 1, further comprising at least one visual cue on the one or more cartridges that indicates the order of use of the cartridges.

11. The procedure kit, according to claim 1, further comprising one more cartridge configured as a waste cartridge.

12. The procedure kit, according to claim 1, further comprising at least one ancillary article configured to engage with the rack.

13. The procedure kit, according to claim 1, further comprising a one-time use unseal mechanism arranged on the unseal flap that is used to unseal the storage compartment..

14. The procedure kit, according to claim 13, wherein the front panel further comprises a reseal flap arranged under the unseal flap, when the storage compartment is sealed, the reseal flap further comprising a reseal mechanism that is secured to a front of the unseal flap to reseal the storage compartment.

15. A method for performing a medical procedure comprising:

A. obtaining a single-use procedure kit, according to claim 1, specific to the medical procedure to be performed,;

B. displacing the top panel with the unseal flap to access the storage compartment;

C. removing from the rack one or more cartridge containing the at least one component for performing a step of the procedure;

D. removing the at least partially removable cover from the cartridge to access the at least one component in the interior space;

E. performing the step of the procedure utilizing the at least one component;

F. replacing the at least partially removable cover on the cartridge to reclose the interior space;

G. repeating steps C through F until the procedure is complete; and

H. replacing the top panel over the storage compartment.

16. The method, according to claim 15, further comprising returning the one or more cartridge to the storage compartment by slidably engaging the flange with the slot-and-landing pair in the rack prior to replacing the top panel.

17. The method, according to claim 16, further comprising returning the one or more cartridge to the same slot-and-landing pair in the rack.

18. The method, according to claim 15, further comprising a visual cue on the one or more cartridge and the method further comprises utilizing the visual cue to determine an order for removing the at least one cartridge and utilizing the one or more components for the procedure.

19. The method, according to claim 15, further comprising at least one cartridge having a depth that is a multiple of the depth of another cartridge, such that at least one wall overlaps at least one slot and is supported by at least two landings.

20. The method, according to claim 15, further comprising at least one cartridge configured as a waste cartridge and the method further comprises depositing biohazard material into the waste cartridge.

21. The method, according to claim 16, further comprising an unseal mechanism on the unseal flap, and the method further comprises using the unseal mechanism to unseal the storage compartment prior to displacing the top flap and the unseal flap to access the storage compartment.

22. The method, according to claim 21, further comprising displacing the front panel to obtain front access to the storage compartment and a front of the rack seat.

23. The method, according to claim 22, further comprising a reseal mechanism and the method further comprises utilizing the reseal mechanism to reseal the storage compartment.

24. The method, according to claim 23, further comprising a reseal flap, extending from the front panel, on which the reseal mechanism is located and the method further comprises arranging the reseal flap over the unseal flap and attaching the reseal mechanism to the unseal flap.

25. The method, according to claim 15, further comprising at least one ancillary article engaged with the rack and the method further comprises removing the ancillary article from the rack.

26. The method, according to claim 15, wherein the at least partially removable cover one or more cartridge is a lidding film and the method further comprises peeling the lidding film from the one or more cartridge to access the interior space.

27. The method, according to claim 26, further comprising a tab on the at least partially removable cover and the method further comprising pulling the tab to peel the lidding film from the at least one cartridge.

28. The method, according to claim 15, further comprising at least one lip on the at least partially removable cover that engages with an interior side surface of the cartridge and the method further comprises disengaging the at least one lip from the interior side surface when removing the at least partially removable cover from the cartridge and reengaging the at least one lip with the interior side surface when replacing the at least partially removable cover on the cartridge.

29. The method, according to claim 22, further comprising slidably engaging the cartridge with the slot-and-landing pair by inserting the flange into the slot at the front of the rack seat.

* * * * *